(12) United States Patent
Blazer et al.

(10) Patent No.: US 9,700,601 B2
(45) Date of Patent: *Jul. 11, 2017

(54) COMPOSITIONS AND METHODS FOR THE TREATMENT OF LYSOSOMAL STORAGE DISORDERS

(71) Applicant: Regents of the University of Minnesota, Minneapolis, MN (US)

(72) Inventors: Bruce Blazer, Golden Valley, MN (US); Jakub Tolar, Minneapolis, MN (US); Catherine M. Verfaillie, Leuven (BE)

(73) Assignee: Regents of The University of Minnesota, Minneapolis, MN (US)

( * ) Notice: Subject to any disclaimer, the term of this patent is extended or adjusted under 35 U.S.C. 154(b) by 351 days.

This patent is subject to a terminal disclaimer.

(21) Appl. No.: 14/064,517

(22) Filed: Oct. 28, 2013

(65) Prior Publication Data

US 2014/0212393 A1    Jul. 31, 2014

Related U.S. Application Data

(63) Continuation of application No. 13/080,109, filed on Apr. 5, 2011, now Pat. No. 8,580,249, which is a continuation of application No. 11/446,560, filed on Jun. 2, 2006, now Pat. No. 7,927,587, which is a continuation of application No. PCT/US2004/040932, filed on Dec. 6, 2004.

(60) Provisional application No. 60/527,249, filed on Dec. 4, 2003.

(51) Int. Cl.
*C12N 5/00* (2006.01)
*A61K 38/47* (2006.01)
*A61K 35/48* (2015.01)
*A61K 38/44* (2006.01)
*C12N 5/074* (2010.01)
*A61K 48/00* (2006.01)

(52) U.S. Cl.
CPC .............. *A61K 38/47* (2013.01); *A61K 35/48* (2013.01); *A61K 38/44* (2013.01); *C12N 5/0607* (2013.01); *A61K 48/00* (2013.01)

(58) Field of Classification Search
None
See application file for complete search history.

(56) References Cited

U.S. PATENT DOCUMENTS 7,927,587 B2 * 4/2011 Blazer .................. C12N 9/2402
424/93.7
8,580,249 B2 * 11/2013 Blazar .................... A61K 35/48
424/93.7

OTHER PUBLICATIONS

Decision on Motions; Patent Interference No. 105,953 SGL, Tech Center 1600; filed Sep. 26, 2014.

* cited by examiner

*Primary Examiner* — Blaine Lankford
(74) *Attorney, Agent, or Firm* — Tarolli, Sundheim, Covell & Tummino LLP

(57) ABSTRACT

The present invention relates to methods for providing lysosomal enzymes to a subject by administering stem cells, preferably Multipotent Adult Progenitor Cells (MAPCs). The invention further relates to methods for treating lysosomal storage disorders by administering stem cells.

7 Claims, 5 Drawing Sheets

SEQUENCE LISTING

```
<160> NUMBER OF SEQ ID NOS: 4

<210> SEQ ID NO 1
<211> LENGTH: 19
<212> TYPE: DNA
<213> ORGANISM: Artificial Sequence
<220> FEATURE:
<223> OTHER INFORMATION: A synthetic oligonucleotide

<400> SEQUENCE: 1
tggattgcac gcaggttct                                                  19

<210> SEQ ID NO 2
<211> LENGTH: 19
<212> TYPE: DNA
<213> ORGANISM: Artificial Sequence
<220> FEATURE:
<223> OTHER INFORMATION: A synthetic oligonucleotide

<400> SEQUENCE: 2
```

```
ttcgcttggt ggtcgaatg                                              19

<210> SEQ ID NO 3
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 3
aaaccagcca tcgccatctg                                             20

<210> SEQ ID NO 4
<211> LENGTH: 24
<212> TYPE: DNA
<213> ORGANISM: Artificial Sequence
<220> FEATURE:
<223> OTHER INFORMATION: A synthetic oligonucleotide

<400> SEQUENCE: 4
ggacaggtcg gtcttgacaa aaag                                        24
```

COMPOSITIONS AND METHODS FOR THE TREATMENT OF LYSOSOMAL STORAGE DISORDERS

REFERENCE TO RELATED APPLICATIONS

This application claims priority under 35 U.S.C. 119(e) from U.S. Provisional Application Ser. No. 60/527,249 filed Dec. 4, 2003, which is incorporated herein by reference.

STATEMENT OF GOVERNMENT RIGHTS

This invention was made with government support under R01-HL049997 awarded by the National Institutes of Health. The government has certain rights in the invention.

FIELD OF THE INVENTION

The present invention relates to methods for providing lysosomal enzymes by administering stem cells, preferably Multipotent Adult Progenitor Cells (MAPCs). The invention further relates to methods for treating lysosomal storage disorders by administering stem cells.

BACKGROUND OF THE INVENTION

Lysosomal storage disorders are a group of more than 40 recessive genetic diseases resulting in deficiencies in lysosomal acid hydrolases (Wraith, J. E., (2001) *Dev. Med. Child. Neural.* 43: 639-646). Although individually rare, lysosomal storage disorders have a prevalence of 1 per 7700 live births. Such diseases include Gaucher's disease, Fabry disease, Niemann-Pick disease, mucopolysaccharidoses Type I through VII, Tay-Sachs disease, among many others. Loss of lysosomal enzyme activity results in the progressive accumulation of undegraded substrate within the lysosomes, resulting in engorgement of the organelle, subsequent cellular, tissue, and organ dysfunction, and often death. Lysosomal storage diseases affect multiple organ systems, many of them before birth, resulting in irreversible defects. Clinical treatments for metabolic storage disorders are limited to bone marrow transplantation and enzyme replacement therapy (Cheng, S. H. and Smith, A. B. (2003) *Gene Ther.* 10: 1275-1281).

Enzyme replacement therapy involves administration of functional lysosomal enzymes to patients. Following administration, the replacement enzymes are secreted by the liver into systemic circulation. Both adjacent and distant cells recapture the secreted enzymes, primarily through the mannose-6-phosphate receptor, which is present on the surface of virtually all cells (Suzuki, K. Lysosomal diseases. In: Graham, D. I., Lantos, P. K. (eds) *Greenfield's Neuropathology*. Arnold: London, (2002) pp. 653-735). Localized administration of enzyme can replenish at least part of the enzyme population in deficient cells. However, these enzymes generally have short circulating and intracellular half-lives, and therapy requires regular parenteral administration of relatively large amounts of the relevant enzyme.

Enzyme replacement therapy is particularly effective when treating certain lysosomal storage diseases. For example, enzyme replacement in the treatment of Gaucher's and Fabry's disease has been effective in reversing non-neuropathic symptoms of these diseases (Weinreb, N. J. et al, (2002) *Am. J. Med.* 113: 112-119; Schiffman, R. et al, (2001) *JAMA* 285: 2743-2749). However, in many lysosomal storage diseases, such as mucopolysaccharidosis type I (i.e., MPS-IH; Hurler's Syndrome), replacement of enzyme can result in potent immunogenic responses against the infused donor proteins. Further, systemically administered enzymes are unable to access sites that arise later in development, such as the CNS and skeletal system. Thus, enzyme replacement therapy is not effective in correcting neurological manifestations and skeletal defects associated with many of these metabolic storage diseases.

Gene targeting has also been used to supply enzymes to patients. However, limited results have been observed thus far. Gene targeting (via targeting vectors, such as lentiviral, retroviral, adenoviral, and adena-associated viral vectors) can result in efficient delivery to target organs, such as lung, liver, or bone marrow (Marshall, J. et al, (2002) *Mol. Ther.* 6: 179-189; Du, H. et al, (2002) *Gene Ther.* 13: 1361-1372). Additionally, intravenous delivery of targeting vectors can result in high-level secretion of the enzymes from the liver and re-uptake in other affected tissues.

However, gene targeting methods also have disadvantages. Expression of the desired enzyme can be transient and decline to basal levels within several weeks. Inflammatory responses mediated by cytotoxic T-lymphocytes against the enzymes have also been observed. Further, correction of more severe defects, such as those residing in the CNS, is unlikely given the difficulties in achieving transfer across the blood-brain barrier, and inducing efficient expression in the quiescent cells of the CNS. In one study, direct intracranial injection using AAV vectors produced only mild correction of cognitive defects in a murine model of mucopolysaccharidosis type VII (MPS VII) (Frisella, W. A. et al., *Mol. Ther.* (2001) 3: 351-358).

Bone marrow transplantation is another potential therapeutic approach to the treatment of lysosomal storage disorders. Bone marrow transplantation reconstitutes a patient's hematopoietic system with stem cells from healthy immunocompatible donors to establish life-long sources of enzyme (Steward, C. G. (1999) Bone marrow transplantation for genetic diseases. In: Fairbairn, L. J., Testa, N. G. (eds) *Blood Cell Biochemistry. Volume 8: Hematopoiesis and Gene Therapy* New York: Kiewer Academic/Plenum Publishers. p. 13-56). Hundreds of patients with lysosomal storage disorders have been treated by transplantation for many years. For example, it has been reported that treatment of non-neuropathic Gaucher's disease by bone marrow transplantation resulted in almost a complete reversal of symptoms (Hoogerbrugge, P. M. et al, (1995) *Lancet* 345: 1398-1402).

Bone marrow transplantation has a more limited effect in the treatment of other lysosomal storage disorders, such as MPS-IH. Bone marrow transplantation can reverse some, but not all of the deleterious effects of the disease (Hoogerbrugge, P. M. et al, supra). If not treated by transplantation, patients will continue to deteriorate due to heparin sulfate and dermatan sulfate glycosaminoglycan accumulation in the cornea, central nervous system, liver, spleen, lungs, heart, muscles, tendons, and bones. The degree of neurological improvement is related to the age of the patient, developmental quotient at the time of transplant, and levels of enzyme obtained following transplantation (Peters, C., et al, (1996) *Blood* 87: 4894-4902; Peters, C. et al, (1998) *Blood* 91: 2601-8). Younger transplant recipients experience clearing of visceral organs, typically with stabilization or slower deterioration of the CNS. Unfortunately, the skeletal system and many CNS defects remain unaffected following transplant.

Results from bone marrow transplantation and enzyme replacement studies demonstrate that most defects, but not all, can be corrected by supplying the patient with enzyme.

However, the failure to correct skeletal and CNS defects in successfully engrafted patients indicates that either there is an insufficient concentration of lysosomal enzymes at the required site (i.e. bone or CNS), or the damage is irreversible. MPS-IH patients typically have <0.13% of normal enzyme levels. However, in patients that are heterozygous for α-L-iduronidase, only 3% of enzyme levels are necessary to yield clinically unaffected leukocytes and fibroblasts (Scott. H. S., et al, (1995) *Hum. Mutat.* 6: 288-302). This suggests that only low levels of replacement enzyme are necessary and that failure to achieve correction of skeletal and CNS manifestations is due to exceedingly low levels of available enzyme in these sites.

Supplying replacement enzymes early in development may result in greater correction of CNS and skeletal abnormalities. Intrauterine transfer, also known as in utero transplantation, offers the earliest opportunity for optimizing correction of irreversible defects that occur during gestation (Flake, A. W. and Zanjani, E. D., (1999) *Blood* 94: 2179-2191). The early gestational fetus is immunologically immature and tolerant to foreign antigen, allowing acceptance of allogeneic or xenogeneic cells without the need for immunosuppression. Therefore, immunologic or metabolic reconstitution is possible before birth.

Although patients with severe immune deficiency disorders can be corrected by intrauterine transfer, those with lysosomal storage disorders have not seemingly benefited from this procedure. Only two patients with MPS-IH treated by IUT have been reported (Donahue, J., and Carrier, E., (2002) *Cancer Treat Res* 110: 177-211). A difference between the results of intrauterine transfer for immune deficiency compared to storage disorders relates to the fact that immunocompetent donor cells (i.e., lymphoid cells) will have a marked competitive proliferative advantage in recipients with immune deficiency disorders. Donor cells (i.e., hematopoietic stem cells (HSCs) or bone marrow mononuclear cells (BMMNCs)) expressing the lysosomal enzyme do not have a proliferative or survival advantage over cells lacking the enzyme.

Animal models of lysosomal storage disorders have confirmed this observation. In a study of MPS VII mice, intrauterine transfer of either syngeneic fetal liver hematopoietic stem cells marked by retroviral vectors, or allogeneic donor cells constitutively overexpressing a human β-glucuronidase ("gus") transgene resulted in only 0.1% engraftment (Casal, M. L., et al, (2001) *Blood* 97: 1625-1634). Enrichment of stem and progenitor cells resulted in significantly higher gus activity at 2 months of age, which delayed the onset of manifestations of the disease, suggesting that expression of the enzyme early in fetal life may slow the progression of the disease. Intrauterine transfer of hematopoietic stem cells or donor fetal liver cells does alleviate GAG storage in tissues, such as cortical neurons and glia (Barker, J. E. et al, (2001) Blood Cells Mol. Dis. 27(5): 861-873), as well as in liver (Casal, M. L. (2000) *Pediatr. Res.* 47(6): 750-756).

The canine model of MPS-IH deficiency was also used to evaluate the therapeutic potential of hematopoietic stem cells infused by intrauterine transfer (Latzko, C., et al, (1999) Hum. Gene Ther. 10: 1521-1532). Autologous marrow cells were genetically modified to express α-L-iduronidase and transferred in utero into preimmune fetal pups. Neither α-L-iduronidase enzyme nor proviral-specific transcripts were detected in blood or marrow leukocytes of any MPS-IH dog. However, the transduced hematopoietic progenitors could engraft in fetal recipients, contribute to hematopoiesis, and induce immunologic nonresponsiveness to α-L-iduronidase. The therapeutic potential of hematopoietic stem cell gene transfer in dogs appeared to be limited by poor maintenance of proviral α-L-iduronidase gene expression and low levels of genetically corrected circulating leukocytes.

Accordingly, a need exists in the art for improved methods for the treatment of lysosomal storage disorders.

SUMMARY OF THE INVENTION

The invention relates to treatment of lysosomal storage disorders by administering stem cells in an amount effective to provide lysosomal enzymes that metabolize substrates in the lysosome of target cells, thereby modulating (e.g., preventing or decreasing) accumulation of the substrates in said cells. Stem cells, preferably Multipotent Adult Progenitor Cells ("MAPCs"), are administered to provide the lysosomal enzymes in vivo. Stem cells for use in the methods of the invention are those that can give rise to cells of endodermal, ectodermal and mesodermal lineages.

Providing the missing or defective enzyme to the tissue or tissues having accumulation of the substrate(s) allows for enzymatic catalysis (i.e., metabolism or break-down) of the substrate, thereby preventing, decreasing or eliminating said accumulation.

Therefore, in one embodiment, the invention is directed to a method for providing a lysosomal enzyme to a subject by administering stem cells to the subject, wherein the stem cells provide a lysosomal enzyme.

In another embodiment, the invention is directed to a method for treating a lysosomal storage disorder by administering stem cells to a subject having a lysosomal storage disorder, wherein the stem cells provide an amount of lysosomal enzyme effective to treat said disorder.

In another embodiment, the invention is directed to modulating accumulation of a substrate in a subject by providing an amount of a lysosomal enzyme to the subject effective to modulate said accumulation, wherein the lysosomal enzyme is provided by stem cells administered to said subject. As used herein, a "substrate" refers to a lysosomal substrate for one or more lysosomal enzymes. Preferably, modulating comprises preventing, decreasing or eliminating accumulation (e.g., levels of accumulation that are undesired and/or that are greater than that of a subject without a lysosomal associated condition) of a substrate.

The lysosomal enzyme of interest can be produced by normal gene expression in stem cells of the invention. In addition, the cells can be genetically modified, for example, to comprise additional copies of a gene encoding a lysosomal enzyme and/or to over-express the endogenous gene.

The lysosomal enzyme can be, but is not limited to, β-galactosidase, hexosaminidase A, hexosaminidase B, $GM_2$-activator, arylsulfatase A, arylsulfatase B, galactosylceramidase, α-galactosidase A, galactosamine-4-sulfatase, α-glucosidase, sphingomyelinase, ceramidase, acid lipase, sulfatases, α-L-iduronidase, iduronate-2-sulfate sulfatase, heparan sulfaminidase, N-acetyl-α-glucosaminidase, α-glucosaminide-N-acetyltransferase (acetyl CoA glucosamine-N-acetyltransferase), N-acetylglucosamine-6-sulfate sulfatase, N-acetylgalactosamine-6-sulfate sulfatase, β-glucuronidase, hyaluronidase, cathepsin K, N-acetyl-β-glucosaminidase, α-fucosidase, α-mannosidase, β-mannosidase, sialic acid transporter, α-N-acetylgalactosamimidase, α-neuraminidase, cathepsin A, N-acetylglucosamine-1-phosphotransferase, α-1,4-glucosidase, palmitoyl protein thioesterase, and/or tripeptidyl peptidase I.

The lysosomal storage disorder can be, but is not limited to, sphingolipidoses, mucopolysaccharidoses, glycoproteinoses, mucolipidoses, glycogenosis type II, and ceroid lipofuscinoses. More specifically, the disorder can be, but is not limited to, GM1 gangliosidosis (Landing's disease), GM2 gangliosidosis variant B/B1 (Tay-Sach's disease) and variant O (Sandhoffs disease), metachromatic leukodystrophy, Krabbe's disease, Fabry's disease, Gaucher's disease, Niemann-Pick disease (A, B, C), Farber's disease, Wolman's disease, Austin's disease, mucopolysaccharidoses type I (Hurler's disease or Hurler's Syndrome), Scheie's disease, Hurler-Scheie's disease, type II (Hunter's disease), type III (Sanfilippo's disease, type III A through D, type IV (Morquio's disease), type IV A and B, type VI (Maroteaux-Lamy's disease), type VII (Sly's disease), type IX, pycnodysostosis, aspartylglucosaminuria, fucosidosis, α-mannosidosis, β-mannosidosis, Schindler's disease, Kanzaki's disease, mucolipidoses type I (sialidosis), type IB (galactosialidosis), and type II, III, and IV (mucolipidoses), Glycogenosis type II (characterized by Pompe's disease), Santavuori-Haltia disease, Jansky-Bielshowsky disease, Batten disease, Kufs disease, disease states characterized by mutations in the CLN5, CLN6, CLN7, and CLN8 loci, and/or other lysosomal storage diseases, such as sialic acid storage diseases (infantile form, Salla disease), and methylmalonic aciduria. In one embodiment the disorder is a mucopolysaccharidosis. In another embodiment the disorder is mucopolysaccharidosis (type I) (e.g., Hurler's disease or Hurler's Syndrome).

The substrate can be, but is not limited to, dermatan sulfate; heparin sulfate; keratan sulfate; hyaluronic acid; sialic acid; $GM_1$-ganglioside; $GM_2$-ganglioside; galactosylceramide; sulfatide; galactosylsphingolipids; glucoceramide; ceramide; sphingomyelin; α-mannoside; β-mannoside; fucoside; aspartylglucosamine; N-acetylgalactosamine; glycogen; cholesterol ester; bone-derived peptides; and/or saponins.

In one embodiment of the present method, the substrate is a glycosaminoglycan. Glycosaminoglycans include, but are not limited to, heparan sulfate, dermatan sulfate, and keratan sulfate. In one embodiment of the invention the enzyme is α-L-iduronidase.

In one embodiment, administration of stem cells or differentiated progeny thereof are administered to an organ of the subject so that the stem cells or the differentiated progeny thereof provide a lysosomal enzyme to said organ.

Preferably, the organ is a visceral organ, including but not limited to, heart, lung, muscle, kidney, spleen, ileum, colon, brain, liver and eye. Preferably, stem cells or the progeny thereof are engrafted into the organ through contact with existing cells of the organ so as to provide the lysosomal enzyme.

Stem cells of the invention (or their progeny) can be administered via localized injection, including by catheter administration, systemic injection, intraperitoneal injection, intraplacental injection, intrauterine injection, intracranial injection, parenteral administration, intraarterial injection and injection into the lateral cerebral ventricles.

In one embodiment, stem cells of the invention are administered to a subject in utero. In utero administration to a subject can be performed by direct injection into the mnbilical vein or liver of the fetus, intraperitoneal injection, intraplacental injection, or intrauterine injection. Preferably, the stem cells of the invention are administered via intraperitoneal injection in the first trimester. In a preferred embodiment, infants are treated by methods of the invention.

Treatment can be by administration of stem cells of the invention to the infant postpartum, or when in utero.

In one embodiment, the stem cells are genetically modified prior to administration of the cells to the subject, for example, to comprise an exogenous gene encoding a lysosomal enzyme and/or to over-express the endogenous gene. In one embodiment of the invention, the exogenous or over-expressed endogenous gene encodes a lysosomal enzyme, including but not limited to β-galactosidase, hexosaminidase A, hexosaminidase B, $GM_2$-activator, arylsulfatase A, arylsulfatase B, galactosylceramidase, α-galactosidase A, galactosamine-4-sulfatase, β-glucosidase, sphingomyelinase, ceramidase, acid lipase, sulfatases, α-L-iduronidase, iduronate-2-sulfate sulfatase, heparan sulfaminidase, N-acetyl-α-glucosaminidase, α-glucosaminide-N-acetyltransferase (acetyl CoA glucosamine-N-acetyl-transferase), N-acetylglucosamine-6-sulfate sulfatase, N-acetylgalactosamine-6-sulfate sulfatase, β-glucuronidase, hyaluronidase, cathepsin K, N-acetyl-α-glucosaminidase, α-fucosidase, α-mmmosidase, β-mmmosidase, sialic acid transporter, α-N-acetylgalactosaminidase, α-neuraminidase, cathepsin A, N-acetylglucosamine-1-phosphotransferase, α-1,4-glucosidase, palmitoyl protein thioesterase, and/or tripeptidyl peptidase I. In another embodiment, the exogenous DNA sequence includes a genetic sequence which codes for a selectable or screenable marker that is expressed so that stem cells with the altered genome, or their progeny can be differentiated from stem cells having an unaltered genome. Examples of markers include, but are not limited to green, red or yellow fluorescent protein, β-galactosidase, neomycin phosphotransferase (NPT), dihydrofolate reductase (DHFRm), or hygromycin phosphotransferase (hpt).

Another embodiment provides for the use of stem cells to prepare a medicament to treat an undesirable accumulation of a substrate for a lysosomal enzyme. In one embodiment, the accumulation of lysosomal enzyme results in a lysosomal storage disorder.

Other aspects of the invention are disclosed in, or are obvious from the following disclosure and are within the ambit of the invention.

BRIEF DESCRIPTION OF THE FIGURES

The following Detailed Description, given by way of example, but not intended to limit the invention to specific embodiments described, may be understood in conjunction with the accompanying drawings, incorporated herein by reference. Various preferred features and embodiments of the present invention will now be described by way of non-limiting examples and with reference to the accompanying drawings, in which.

DETAILED DESCRIPTION OF THE INVENTION

Definitions

Figure 1:
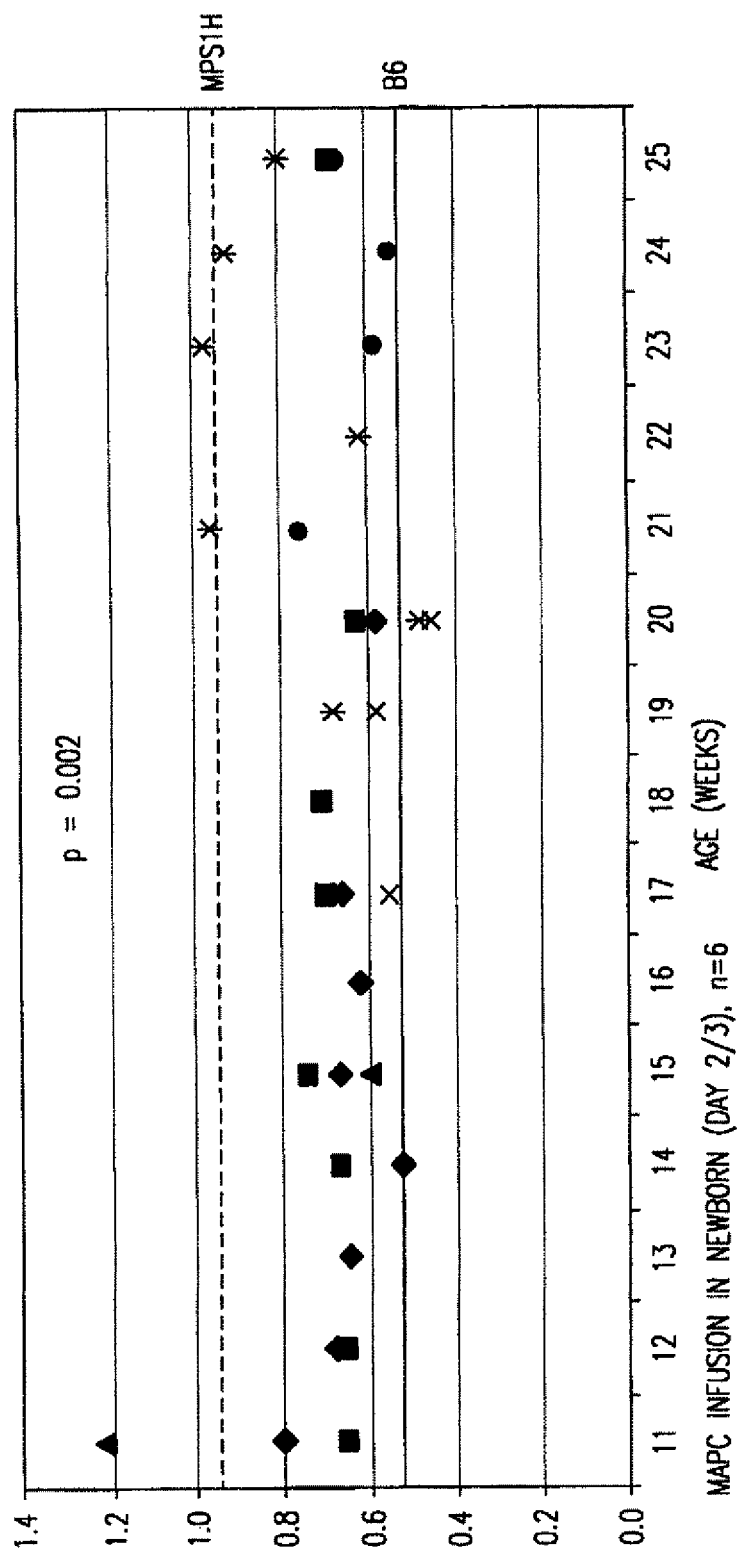
FIG. 1 is a graph depicting a decrease in GAG levels in urine of B6 and MPS-1H mice receiving in utero MAPC infusion.

As used herein, the terms below are defined by the following meanings:

"Stem cell" refers to a cell that can give rise to cells of endodermal, ectodermal and mesodermal lineages. A "MAPC" is one type of stem cell. Another is an "embryonic stem cell."

"Germ layers" are the three primary layers formed as a result of gastrulation in early stage embryos, consisting of endoderm, mesoderm and ectoderm. Embryonic germ layers are the source from which all tissues and organs derive. The endoderm is the source of, for example, pharynx, esophagus, stomach, intestine and associated glands (e.g., salivary glands), liver, epithelial linings of respiratory passages and gastrointestinal tract, pancreas and lungs. The mesoderm is the source of, for example, smooth and striated muscle, connective tissue, vessels, the cardiovascular system, blood cells, bone marrow, skeleton, reproductive organs and excretory organs. Ectoderm is the source of, for example, epidermis (epidermal layer of the skin), sensory organs, the entire nervous system, including brain, spinal cord, and all the outlying components of the nervous system.

"MAPC" is an acronym for a multipotent adult progenitor cell. It refers to a multipotent non-ES, non-EG, non-germ cell that is capable of self renewal and that can give rise to cells of all three primitive germ layers (endoderm, mesoderm and ectoderm) upon differentiation. See PCT/US00/21387, published as WO 01/11011, and filed as U.S. application Ser. No. 10/048,757 (specifically incorporated by reference for the description of MAPC isolation, characterization and preparation) and PCT/US02/04652, published as WO 02/064748, and filed as U.S. application Ser. No. 10/467,963 (specifically incorporated by reference for the description of MAPC isolation, characterization and preparation). Like embryonic stem cells, MAPCs express a number of cell markers designating them as a primitive cell type. For example, human MAPCs have been tested for and express Oct-3/4, Rex-1, Rox-1, Sox-2 and populations of MAPC express SSEA-4.

"Multipotent" with respect to MAPCs refers to the ability to give rise to cells of all three primitive germ layers (endoderm, mesoderm, and ectoderm) upon differentiation.

"Progenitor cells" are cells produced during differentiation of a stem cell that have some, but not all, of the characteristics of their terminally differentiated progeny. Defined progenitor cells are committed to a lineage, but not to a specific or terminally differentiated cell type. The term "progenitor" as used in the acronym "MAPC" does not limit these cells to a particular lineage.

"Enriching" means that the cells of one type are increased over the cells of another type in the starting culture or preparation.

"Isolated" refers to a cell which is not associated with one or more cells or one or more cellular components that is associated with the cell in vivo. For example, an isolated population of cells may be a population of cells purified to various percentages as indicated herein below.

A "subject" is a vertebrate, preferably a mammal, more preferably a human. Subjects of the invention can be, but are not limited to unborn (e.g., a fetus or embryo) or newborn subjects. Mammals include, but are not limited to, humans, farm animals, sport animals, and pets.

"Treat" or "treating" includes treating, preventing, ameliorating, or inhibiting physical or disease related damage and/or a symptom of physical or disease related damage of a subject. Additionally, "treat" or "treating" includes treating, preventing, ameliorating, or inhibiting undesired accumulation of a substrate in a subject.

"Effective amount" means an amount which provides the desired local or systemic effect. For example, an effective dose is an amount sufficient to effect a beneficial or desired clinical or non-clinical result.

As used herein, a subject receiving a lysosomal enzyme, who is "in need Thereof" is a subject having a lysosomal storage disorder or at risk of developing a lysosomal storage disorder. Additionally, a subject receiving a lysosomal enzyme, who is "in need thereof" is a subject having undesirable amounts of substrate.

A "lysosomal storage disorder" is any disorder where the existence or accumulation of a lysosomal enzyme substrate occurs due to a deficiency in a lysosomal enzyme, such that an undesired effect is produced (e.g., abnormal accumulation of substrate or production of an abnormal substrate). The lysosomal enzyme may be produced in abnormal amounts (e.g., the enzyme may not be expressed at all in a subject, may be expressed at low levels or may be expressed at high levels) or may function abnormally, for example, due to a mutation or improper protein folding.

A "lysosomal enzyme" is any hydrolytic enzyme contained in the lysosomal compartment of a cell that metabolizes cellular byproducts contained therein.

As used herein, a "substrate" refers to a lysosomal substrate for one or more lysosomal enzymes.

"Modulating accumulation of substrate" is regulating the amount of an un-metabolized or improperly metabolized substrate of a lysosomal enzyme. Modulation includes decreasing, eliminating or preventing accumulation of a substrate (e.g., accumulation of substrate resulting in a lysosomal storage disorder as well as accumulation of substrate that is not pathogenic, but is not at a desired level for the subject).

"Engraft" refers to the process of stem cell incorporation into a tissue of interest in vivo through contact with existing cells of the tissue.

"Differentiation factors" refer to cellular factors, preferably growth factors or angiogenic factors that induce lineage commitment. A similar term used in this context is "cytokine". Cytokines can also refer to cellular factors that induce or enhance cellular movement, such as homing of MAPCs or other stem cells of the invention, progenitor cells or differentiated cells and the like.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not deleteriously changed by the presence of more than that which is recited.

Other definitions may appear throughout this disclosure in the appropriate context.

Methods of the Invention

In one embodiment, the invention is directed to a method for treating a lysosomal storage disorder by administering stem cells of the invention to a subject in need thereof, so that the stem cells of the invention provide an amount of a lysosomal enzyme effective to modulate undesired substrate accumulation in cells of said subject. Preferably, the stem cells are MAPCs.

Lysosomal storage disorders of the invention can be subdivided into the following disease states: sphingolipidoses, mucopolysaccharidoses, glycoproteinoses, mucolipidoses, glycogenesis type II, ceroid lipofuscinoses, and those that fall under the category of "other" (Caillaud, C. et al., (2000) *Biomed. Pharmaeother.* 54: 505-12; Nathan and Oski's Hematology of Infancy and Childhood, (2003) Chapter 35, W.B. Saunders). Nearly all lysosomal storage disorders are autosomal recessive. Two noted exceptions to this are Fabry's Disease and Hunter's Syndrome, which are X-linked.

Sphingolipidoses comprise the following diseases, but are not limited to these diseases: GM1 gangliosidosis (Landing's disease; β-galactosidase deficiency), GM2 gangliosidosis variant B/B1 (Tay-Sach's disease; hexosaminidase A deficiency) and variant O (Sandhoff's disease, hexosaminidase A and B deficiency), metachromatic leukodystrophy (arylsulfatase A deficiency), Krabbe's disease (galactosylceramidase deficiency), Fabry's disease (α-galactosidase deficiency), Gaucher's disease (deficiency in β-glucosidase), Niemann-Pick disease (A, B, C; sphingomyelinase deficiency), Farber's disease (deficiency in ceramidase), Wolman's disease (deficiency in acid lipase), and Austin's disease (deficiency in multiple sulfatases).

Mucopolysaccharidoses comprise the following diseases, but are not limited to: type I (Hurler's disease or Hurler's Syndrome), Scheie's disease (deficiency in α-L-iduronidase), Hurler-Scheie's disease, type II (Hunter's disease; iduronate-2-sulfate sulfatase deficiency), type III (Sanfilippo's disease, type III A through D (deficiency in heparan sulfamidase, N-acetyl-α-glucosaminidase, α-glucosaminide-N-acetyltransferase, or N-acetylglucosamine-6-sulfate sulfatase deficiency, respectively), type IV (Morquio's disease), type IV A (N-acetylgalactosamine-6-sulfate sulfatase deficiency) and B (β-galactosidase deficiency), type VI (Maroteaux-Lamy's disease; arylsulfatase B deficiency), type VII (Sly's disease; β-glucuronidase deficiency), type IX (hyaluronidase deficiency), and pycnodysostosis (cathepsin K deficiency).

Glycoproteinoses comprise the following diseases, but are not limited to these diseases: aspartylglucosaminuria (deficiency in N-acetyl β-glucosaminidase), fucosidosis (deficiency in α-fucosidase), α-mannosidosis α-mannosidase deficiency), β-mannosidosis (β-mannosidase deficiency), Schindler's disease, and Kanzaki's disease (α-N-acetylgalactosaminidase or α-galactosidase B, for both Schindler's and Kanzaki's disease).

Mucolipidoses comprise the following, but are not limited to, diseases: type I (sialidosis; α-neuraminidase deficiency), type TB (galactosialidosis; Cathepsin A deficiency), and type II, III, and IV (mucolipidoses; N-acetylglucosamine-1-phosphotransferase). Glycogenesis type II is characterized, for example, by Pompe's disease (deficiency in α-1, 4-glucosidase or acid maltase).

Ceroid lipofuscinoses comprise, for example, Santavuori-Haltia disease (palmitoyl protein thioesterase deficiency), Jansky-Bielshowsky disease (tripeptidyl peptidase I deficiency), Batten disease (CLN3 protein deficiency). Kufs disease, and disease states characterized by mutations in the CLN5, CLN6, CLN7, and CLN8 loci.

Other lysosomal storage diseases include, but are not limited to, sialic acid storage diseases (infantile form, Salla disease; deficient in sialic acid carrier), and methylmalonic aciduria (deficient in vitamin B12 carrier protein).

A mucopolysaccharidosis is amenable to treatment by the present method, e.g., mucopolysaccharidosis type I (Hurler's disease or Hurler's Syndrome).

The lysosomal enzyme can be, but is not limited to β-galactosidase, hexosaminidase A, hexosaminidase B, $GM_2$-activator, arylsulfatase A, arylsulfatase B, galactosylceramidase, α-galactosidase A, galactosamine-4-sulfatase, β-glucosidase, sphingomyelinase, ceramidase, acid lipase, sulfatases, α-L-iduronidase, iduronate-2-sulfate sulfatase, heparan sulfaminidase, N-acetyl-α-glucosaminidase, α-glucosaminide-N-acetyltransferase (acetyl CoA glucosamine-N-acetyltransferase), N-acetylglucosamine-6-sulfate sulfatase, N-acetylgalactosamine-6-sulfate sulfatase, β-glucuronidase, hyaluronidase, cathepsin K, N-acetyl-β-glucosaminidase, α-fucosidase, α-mannosidase, mannosidase, sialic acid transporter, α-N-acetylgalactosaminidase, α-neuraminidase, cathepsin A, N-acetylglucosamine-1-phosphotransferase, α-1,4-glucosidase, palmitoyl protein thioesterase, and tripeptidyl peptidase I. In one embodiment, the enzyme is α-L-iduronidase.

In one embodiment, administration of stem cells of the invention, or the differentiated progeny thereof, is directly to one or more organs deficient, in amount and/or function, in one or more lysosomal enzymes. Methods of the invention are well suited for delivery of lysosomal enzymes to visceral organs, including but not limited to heart, lung, muscle, kidney, spleen, ileum, colon, brain, liver and eye. Methods of the invention can also provide lysosomal enzymes to non-visceral organs, such as the skeletal system and the CNS. Preferably, stem cells of the invention are engrafted (i.e., incorporated into the organ(s) upon contact with existing cells of the organ(s)), thereby providing a needed lysosomal enzyme to the subject. Lysosomal enzymes are secreted by the stem cells of the invention, and taken up by native cells, for example, by endocytosis, receptor-mediated uptake, and/or pinocytosis.

For example, in mucopolysaccharidoses, specific lysosomal hydrolytic enzymes in the lysosomal compartment, present in all cells of the body, are inactive. Normally, each enzyme would function as a hydrolase with high specificity for a particular chemical bond in its substrate. Glycosaminoglycans (which are normally degraded by the enzyme) accumulate in the cells of subjects suffering from mucopolysaccharidoses and injure the architecture and function of the cells. According to methods of the invention, stem cells of the invention that express the enzyme release lysosomal hydrolases. Surface receptors of surrounding cells, such as fibroblasts, can pick up the enzyme via recognition of its carbohydrate moiety. In particular, α-L-iduronidase is secreted by stem cells of the invention, and is active without further systemic processing.

Enzyme levels can be monitored in subjects treated by methods of the invention according to methods known to the art. In general, the preferred method for enzyme detection is a substrate assay. A substrate assay can comprise, for example, assessing the activity of an enzyme using a substrate, which upon the direct action of the enzyme releases a dye in linear fashion, and which is in turn quantified colorimetrically. The presence of a replacement enzyme in a subject treated by methods of the invention can also be detected by measurements of enzyme mRNA (e.g., reverse transcriptase PCR or Northern blotting), or by detection of the enzyme in the cellular lysate (e.g., Western blotting).

The substrate can be, but is not limited to, dermatan sulfate (metabolized by α-L-iduronidase, iduronate-2-sulfatase, galactosamine-4-sulfatase and/or β-glucuronidase); heparin sulfate (metabolized by α-L-iduronidase, iduronate-2-sulfatase, heparan sulfamidase, N-acetyl-α-glucosaminidase, acetyl CoA. glucosamine-N-acetyltransferase, N-acetylglucosamine-1-phosphotransferase, N-acetylglucosamine-6-sulfate sulfatase and/or β-glucuronidase); keratan sulfate (metabolized by N-acetylgalactosamine-6-sulfate sulfatase and/or βgalactosidase); hyaluronic acid (metabolized by hyaluronidase); sialic acid (metabolized by neuraminidase and/or sialic acid transporter); $GM_1$-ganglioside (metabolized by β-galactosidase); GM2-ganglioside (metabolized by β-hexosaminidase A, β-hexosaminidase B, $GM_2$ activator); galactosylceramide (metabolized by galactosylceramidase); sulfatide (metabolized by arylsulfatase A and B); galactosylsphingolipids (metabolized by α-galactosidase A); glucoceramide (metabolized by β-glucosidase), ceramide (metabolized by ceramidase); sphingomyelin (metabolized by sphingomyelinase); α-mannoside (metabolized by α-malmosidase); β-mannoside (metabolized by β-mannosidase); fucoside (metabolized by fucosidase); N-acetyl-β-glucosamine (metabolized by N-acetyl-β-glucosaminidase); N-acetylgalactosamine (metabolized by α-galactosidase, α-N-acetylgalactosaminidase); glycogen (metabolized by α-glucosidase); cholesterol ester (metabolized by acid lipase); bone-derived peptides (metabolized by cathepsin K); galactosialic acid (metabolized by cathepsin A); and saponins (metabolized by palmitoyl protein thioesterase).

Tables 1-6 are provided below as an overview of lysosomal storage diseases, their associated enzymes, and corresponding substrates.

TABLE 1

Sphingolipidoses

| Disorder | Enzyme | Substrate |
|---|---|---|
| $GM_1$-gangliosidosis Landing's Disease | β-galactosidase | $GM_1$-ganglioside |
| $GM_2$-gangliosidosis variant B/B1 Tay-Sachs Disease | Hexosarninidase A | GMrganglioside |
| $GM_2$-gangliosidosis variant O | Hexosarninidase A | $GM_2$-ganglioside |
| Sandhoff's Disease | Hexosarninidase B | |
| Metachromatic leukodystrophy | Arylsulfatase A | Sulfatide |
| Krabbe's Disease | Galactosylcerarnidase | Galactosylceramide |
| Fabry's Disease | α-galactosidase | Galactosylsphingolipids |
| Gaucher's Disease | β-glucosidase | Glucoceramide |
| Niemann-Pick's Disease variants A, B, C | Sphingomyelinase | Sphingomyelin |
| Farber's Disease | Ceramidase | Ceramide |
| Wolman's Disease | Acid lipase | Cholesterol ester |
| Austin's Disease | Multiple sulfatases | Sulfatide |

TABLE 2

Muco_polysaccharidoses

| Disorder | Enzyme | Substrate |
|---|---|---|
| Type I Hurler's Disease | α-L-iduronidase | Heparan sulfate Dermatan sulfate |
| Scheie's Disease | α-L-iduronidase | Heparan sulfate Dermatan sulfate |
| Hurler-Scheie's Disease | α-L-iduronidase | Heparan sulfate Dermatan sulfate |
| Type II Hunter's Disease | Iduronate-2-sulfate sulfatase | Heparan sulfate Dermatan sulfate |
| Type III Sanfilippo's Disease variants A, B, C, D | A: heparan sulfamidase B: N-acetyl-α-glucosaminidase C: α-glucosaminide-N-acetyltransferase D: N-acetylglucosamine-6-sulfate sulfatase | A-D: heparan sulfate |
| Type IV Morquio's Disease A, B | A: N-acetylgalactosamine-6-sulfate sulfatase B: β-galactosidase | A, B: keratan sulfate |
| Type VI Maroteaux-Lamy's Disease | Arylsulfatase B | Sulfatide |
| Type VII Sly's Disease | β-glucuronidase | Dermatan sulfate Heparan sulfate |
| Type IX Pycnodysostosis | Hyaluronidase CathepsinK | Hyaluronic acid Bone-derived peptides |

TABLE 3

Glycoproteinoses

| Disorder | Enzyme | Substrate |
|---|---|---|
| Aspartylglucosaminuria | N-acetvl β-glucos-aminidase | N-acetvl-β-glucosamine |
| Fucosidosis | α-fucosidase | Fucoside |
| α-mannosidosis | α-mannosidase | α-mannoside |
| β-mannosidosis | β-rnannosidase | β-rnannoside |
| Schindler's Disease | α-N-acetvlgalactos-aminidase | N-acetylgalactosarnine |
| Kanzaki's Disease | α-galactosidase B | N-acetylgalactosarnine |

TABLE 4

Mucolipidoses

| Disorder | Enzyme | Substrate |
|---|---|---|
| Type I Sialidosis | α-neuraminidase | Sialic acid |
| TypeiB Galactosialidosis | Cathepsin A | Galactosialic acid |
| Types II, III, IV | N-acetylglucosamine-1-phosphotransferase | Heparin sulfate |

TABLE 5

Ceroid Lipofuscinoses

| Disorder | Enzyme | Substrate |
|---|---|---|
| Santavuori-Haltia Disease | Palmitoyl protein thioesterase | Saposins |
| Jansky-Bielshowsky Disease | Tripeptidyl peptidase I | Unknown |
| Batten Disease | CLN3 protein | Unknown |
| Kufs Disease | Unknown | Unknown |
| Uncharacterized | CLNS, CLN6, CLN7, CLN8 | Unknown |

TABLE 6

Other

| Disorder | Enzyme | Substrate |
|---|---|---|
| Glycogenosis type II Pompe's Disease | α-1,4-glucosidase acid maltase | Glycogen |
| Sialic acid storage diseases Infantile form Salla's disease | Sialic acid carrier | Sialic acid |
| Methylmalonic aciduria | VitaminB12 carrier | methylmalonate | i. Methods of Decreasing or Preventing Glycosaminoglycan Accumulation

In one embodiment the invention is directed to modulating accumulation of glycosaminoglycans by providing a lysosomal enzyme, whereby the lysosomal enzyme is provided by a stem cell. For example, the enzyme can be α-L-iduronidase.

Accumulation of glycosaminoglycans can be modulated by providing a lysosomal enzyme that includes, but is not limited to β-galactosidase, hexosaminidase A, hexosaminidase B, $GM_2$-activator, arylsulfatase A, arylsulfatase B, galactosylceramidase, α-galactosidase A, galactosamine-4-sulfatase, β-glucosidase, sphingomyelinase, ceramidase, acid lipase, sulfatases, α-L-iduronidase, iduronate-2-sulfate sulfatase, heparan sulfaminidase, N-acetyl-α-glucosaminidase, α-glucosaminide-N-acetyltransferase (acetyl CoA glucosamine-N-acetyltransferase), N-acetylglucosamine-6-sulfate sulfatase, N-acetylgalactosamine-6-sulfate sulfatase, β-glucuronidase, hyaluronidase, cathepsin K, N-acetyl-β-glucosaminidase, α-fucosidase, α-mannosidase, βmannosidase, sialic acid transporter, α-N-acetylgalactosaminidase, α-neuraminidase, cathepsin A, N-acetylglucosamine-1-phosphotransferase, α-1,4-glucosidase, palmitoyl protein thioesterase, and tripeptidyl peptidase I.

In another embodiment, the invention is directed to a method for treating or preventing mucopolysaccharidoses (e.g., Hurler's disease (also referred to as Hurler's Syndrome)) by administering stem cells of the invention.

In another embodiment, the invention is directed to a method of modulating accumulation of glycosaminoglycans in one or more organs deficient in one or more lysosomal enzymes, comprising providing a stem cell, or the differentiated progeny thereof, to the organ(s). The organ can be, but is not limited to, visceral organs, such as heart, lung, muscle, kidney, spleen, ileum, colon, brain, liver and eye. Lysosomal enzymes can also be provided to non-visceral organs, such as the skeletal system and the CNS.

ii. Methods of Detecting Glycosaminoglycan (GAG) Accumulation

The presence of glycosaminoglycan accumulation in tissues of interest can be detected using calorimetric assays, such as colorimetric assays for creatinine, or using dimethylmethylene blue dye. Lysosomal storage diseases are a function of enzyme activity, if any. Therefore, GAG accumulation can be generally thought of as a decrease, reduction, or amelioration of the lysosomal enzyme expression or activity. This can be measured by providing a purified enzyme, such as α-L-iduronidase ("IDUA"), with its physiological substrate such as chondroitin sulfate or dermatan sulfate; or with a synthetic substrate such as 4-methylumbelliferone, and measuring the enzyme activity by colorimetric or fluorescence assay. Color change can be detected, for example, on a spectrophotometer, while fluorescence can be measured in a spectrofluorimeter, wherein the spectrofluorimeter detects the excitation and emission wavelengths of the product.

Glycosaminoglycans can also be accurately measured with thin-layer chromatography, gas-liquid chromatography, or they can be precipitated with quaternary ammonium salts and fractionated by electrophoresis. Expression of lysosomal enzymes such as IDUA can be detected using standard protocols like RT-PCR, Western Blotting, ELISA, and immunohistochemistry, among others. Supportive data can be obtained from the measurements of mRNA of the enzyme, for example, by RT-PCR or Northern Blotting, and from detection of the protein in the cellular lysate, for example, by Western Blotting. However, it is preferable to detect enzyme activity using the aforementioned colorimetric assays, as the direct action of the enzyme releases a dye in linear fashion, which is in turn quantified colorimetrically.

iii. Stem Cells

Stem cells are defined as cells that have extensive, possibly indefinite, proliferation potential, that differentiate into more than one cell lineage, and that repopulate tissues upon transplantation. The quintessential stem cell is the embryonal stem (ES) cell, as it has unlimited self-renewal and can differentiate into all tissue types. ES cells are derived from the inner cell mass of the blastocyst, or primordial germ cells from a post-implantation embryo (embryonal germ cells or EG cells). ES and EG cells have been derived from mouse, and more recently also from non-human primates and humans. When introduced into mouse blastocysts or blastocysts of other animals, ES cells can contribute to all tissues of the mouse (animal). When transplanted in post-natal animals, ES and EG cells generate teratomas. ES (and EG)

cells can be identified by positive staining with the antibodies SSEA1 (mouse) and SSEA4 (human).

At the molecular level, ES and EG cells express a number of transcription factors highly specific for these undifferentiated cells. These include act-4 and rex-1. Also found are the LIF-R and the transcription factors sox-2 and rox-1. Rox-1 and sox-2 are also expressed in non-ES cells. The Oct-4 gene (Oct-3 in humans) is transcribed into at least two splice variants in humans, Oct3A and Oct3B. The Oct3B splice variant is found in many differentiated cells whereas the Oct3A splice variant (previously designated Oct3/4) is reported to be specific for the undifferentiated embryonic stem cell.

Oct-4 (Oct 3 in humans) is a transcription factor expressed in the pregastrulation embryo, early cleavage stage embryo, cells of the inner cell mass of the blastocyst, and in embryonic carcinoma (EC) cells (Nichols J, et al *Cell* 95:379-91, 1998), and is down-regulated when cells are induced to differentiate. Expression of Oct-4 plays a role in determining early steps in embryogenesis and differentiation. Oct-4, in combination with Rox-1, causes transcriptional activation of the Zn-finger protein Rex-1, also required for maintaining ES undifferentiated (Rosfjord E, Rizzino A. *Biochem Biophys Res Commun* 203:1795-802, 1997; Ben-Shushan E, et al, *Mol Cell Biol* 18:1866-78, 1998). In addition, Sox-2, expressed in ES/EC, but also in other more differentiated cells, is needed together with Oct-4 to retain the undifferentiated state of ES/EC (Uwanogho D, Rex M, Cartwright E J, Pearl G, Healy C, Scotting P J, Sharpe P T, *Mech Dev.*, 49:23-36 (1995)). Maintenance of murine ES cells and primordial germ cells requires presence of LIP whereas this requirement is not so clear for human and non-human primate ES cells.

Stem cells for use in carrying out methods of the present invention refer to cells that can give rise to cell lineages derived from all three germ layers. Preferably, the stem cell is a MAPC. Other stem cells known in the art, such as those described herein, are also desirable for use.

"MAPC" refers to a cell that is derived from non-embryonic tissue but which can give rise to cell lineages of all three germ layers (i.e., endoderm, mesoderm, and ectoderm) upon differentiation in vitro or in vivo-hence the definition of lineage pluripotency. In this context, they are equivalent to embryonal stem cells, and distinct from mesenchymal stem cells, which are also isolated from bone marrow. The biological potency of these cells has been proven in various animal models, including mouse, rat, and xenogeneic engraftment of human stem cells in rats or NOD/SCID mice (Reyes, M. and C. M. Verfaillie (2001) *Ann N.Y. Acad. Sci.*, 938:231-3; discussion 233-5; Jiang, Y., et al. (2002) *Exp Hematol.*, 30(8):896-904). In an elegant demonstration of the clonal potency of this cell population, single genetically marked MAPC were injected into mouse blastocysts, blastocysts implanted, and embryos developed to term (Jiang, Y., et al. (2002) *Nature*, 418(6893):41-9). Post-natal analysis in highly chimeric animals shows reconstitution of all tissues and organs, including liver. Dual staining experiments demonstrate that gene marked stem cells contribute to a significant percentage of apparently functional cardiomyocytes in these animals. These animals did not show any heart abnormalities or irregularities in either embryological or adult states. No abnormalities or organ dysfunction were observed in any of these animals.

This cell has been extensively characterized in U.S. patent application Ser. Nos. 10/048,757 and 10/467,963, the contents of which are incorporated by reference for the description of MAPCs and the isolation thereof, especially from human tissue. MAPCs have been extensively characterized with respect to cell surface marker expression, and are negative for cell surface expression of GlyA, CD44, CD45 and HLA.

Biologically and antigenically distinct from MSC, MAPC represents a more primitive progenitor cell population than the MSC and demonstrates differentiation capability encompassing the epithelial, endothelial, neural, myogenic, hematopoeitic, osteogenic, hepatogenic, chondrogenic and adipogenic lineages (Verfaillie, C. M. (2002) *Trends Cell Biol.*; 12(11): p. 502-8, Jahagirdar, B. N., et al. (2001) *Exp Hematol.*, 29(5): p. 543-56). MAPCs thus represent a new class of adult stem cell that emulate the broad biological plasticity characteristic of ES cells, while maintaining the other characteristics that make adult stem cells appealing. For example, MAPC are capable of indefinite culture without loss of their differentiation potential and show efficient, long term engraftment and differentiation along multiple developmental lineages in NOD-SCID mice without evidence of teratoma formation (Reyes, M. and C. M. Verfaillie (2001) *Ann NY Acad Sci.*, 938: p. 231-3; discussion 233-5). The ability to escape replicative senescence, similar to ES cells, and a property not found in other adult stem cell types, is a key component in cell expansion strategies to use these cells for clinical or research use.

MAPCs were initially isolated from bone marrow but subsequently established from other tissues, including brain, muscle, and cord blood (Jiang, Y., et al. (2002) *Exp. Hematol.*, 30(8): p. 896-904). Adherent cells from bone tissue are enriched in a media containing low serum (2%), dexamethasone, EGF, PDGF, and other additives, and grown to high population doublings. At early culture points, more heterogeneity is detected in the population, but many adherent stromal cells undergo replicative senescence around cell doubling 30, and a more homogenous population of cells continues to expand, and maintains long telomere length.

Human MAPCs are described in U.S. application Ser. No. 10/048,757 (see page 8, lines 23-32; p. 9, lines 1-22; p. 21, lines 19-32; p. 22, lines 1-27; p. 25, lines 20-31; pages 26 through p. 28, lines 1-13, 20-25; p. 29, lines 1-21) and U.S. application Ser. No. 10/467,963 (see p. 9, lines 29-32; p. 10, lines 1-25), specifically incorporated by reference for the characterization of MAPCs.

MAPCs are further characterized as cells that constitutively express Oct-4 and high levels of telomerase (Jiang, Y. et al, (2002) *Nature*, 418: 41-49). MAPCs derived from human, mouse, rat or other mammals appear to be the only normal, non-malignant, somatic cells (i.e., non-germ cells) known to date to express very high levels of telomerase even in late passage cells. The telomeres are extended in MAPCs and they are karyotypically normal. MAPCs injected into a mammal can migrate to and assimilate within multiple organs. MAPCs are self-renewing stem cells. As such, they have utility in the repopulation of organs, either in a self-renewing state or in a differentiated state compatible with the organ of interest. They have the capacity to replace cell types that could have been damaged, died, or otherwise might have an abnormal function because of genetic or acquired disease.

MAPCs have been identified in other mammals. Murine MAPCs, for example, are also described in U.S. application Ser. No. 10/048,757 (see p. 28, lines 15-18) and U.S. application Ser. No. 10/467,963 (see p. 22, lines 25-32; p. 23, lines 1-32), specifically incorporated by reference for the description of murine MAPCs.

Methods of MAPC isolation are described in U.S. application Ser. No. 10/048,757 (p. 10, lines 17-32; p. 11, lines 1-12; p. 22, lines 29-32; p. 23, lines 1-32; p. 24, lines 1-28; p. 71, lines 28-32; p. 72 through p. 74, lines 1-27) and U.S. application Ser. No. 10/467,963 (p. 26, lines 13-34; p. 27 through p. 28, lines 1-27), specifically incorporated by reference for the methods of isolation described.

MAPCs can be isolated from multiple sources, including bone marrow, muscle, brain, spinal cord, blood, including umbilical cord blood, or skin. To isolate MAPCs, bone marrow mononuclear cells can be derived from bone marrow aspirates, which can be obtained by standard means known to those of skill in the art (sec, for example, Muschler, G. F., et al., (1997) *J. Bone Joint Surg. Am.,* 79(11): 1699-709; Batinic, D., et al., (1990) *Bone Marrow Transplant.,* 6(2): 103-7).

MAPCs are present within the bone marrow (or other organs, such as liver and brain), but do not express the common leukocyte antigen. CD45 or erythroblast specific glycophorin-A (GlyA). The mixed population of bone marrow cells can be subjected to a Ficoll Hypaque separation. Cells can then be subjected to negative selection using anti-CD45 and anti-GlyA antibodies, depleting the population of $CD45^+$ and $GlyA^+$ cells, and recovering the remaining approximately 0.1% of marrow mononuclear cells. Cells can also be plated in fibronectin-coated wells and cultured as described below for 2-4 weeks after which the cells are depleted of $CD45^+$ and $GlyA^+$ cells.

Alternatively, positive selection can be employed to isolate cells using a combination of cell-specific markers, such as the leukemia inhibitory factor (LIF) receptor. Both positive and negative selection techniques are known to those of skill in the art, and numerous monoclonal and polyclonal antibodies suitable for negative selection purposes are also known in the art (see, for example, Leukocyte Typing V, Schlossman, et al., Eds. (1995) Oxford University Press) and are commercially available from a number of sources.

Techniques for mammalian cell separation from a mixture of cell populations have also been described by Schwartz, et al., in U.S. Pat. No. 5,759,793 (magnetic separation), Basch, et al., (1983) *J. Immunol. Methods* 56: 269 (immunoaffinity chromatography), and Wysocki and Sato, *Proc. Natl. Acad. Sci.* (USA) (1978) 75: 2844 (fluorescence-activated cell sorting).

Methods of MAPC culture are described in U.S. application Ser. No. 10/048,757 (p. 23, lines 25-32) and U.S. application Ser. No. 10/467,963 (p. 26, lines 18-29), specifically incorporated by reference for the culture methods described.

Recovered CD45−/GlyA cells can be plated onto culture dishes coated with 5-ng/ml (preferably about 7-10 ng/ml) serum fibronectin or other appropriate matrix coating. Cells can be maintained in Dulbecco Minimal Essential Medium (DMEM) or other appropriate cell culture medium, supplemented with 10 ng/ml (preferably about 5-15 ng/ml) platelet-derived growth factor-BB (PDGF-BB), 1-50 ng/ml (preferably about 5-15 ng/ml) epidermal growth factor (EGF), 1-50 ng/ml (preferably about 5-15 ng/ml) insulin-like growth factor (IGF), or 100-10,000 IU (preferably about 1,000 IU) LIF, with 100 to $10^{-8}$M dexamethasone or other appropriate steroid, 2-10 µg/ml linoleic acid, and 0.05-0.15 µM ascorbic acid. Other appropriate media include, for example, MCDB, MEM, IMDM, and RPML. Cells can either be maintained without serum, in the presence of 1-2% fetal calf serum, or, for example, in 1-2% human AB serum or autologous serum. The density at which the cells are cultured can vary from about 500/cm² to 10,000/cm². Below about 500/cm² cells do not grow well and begin to undergo apoptosis. Above 10,000/cm² cells begin to lose multipotency. Preferred maintenance density is around 2,000 cells/cm².

An issue regarding the use of stem cells is the purity of the isolated stem cell population. Bone marrow cells, for example, comprise mixed populations of cells, which can be purified to a degree sufficient to produce a desired effect. Those skilled in the art can readily determine the percentage of MAPCs in a population using various well-known methods, such as fluorescence activated cell sorting (FACS). Preferable ranges of purity in populations comprising MAPCs are about 50-55%, 55-60%, and 65-70%. More preferably the purity is about 70-75%, 75-80%, 80-85%; and most preferably the purity is about 85-90%, 90-95%, and 95-100%. However, populations with lower purity can also be useful, such as about 25-30%, 30-35%, 35-40%, 40-45% and 45-50%. Purity of MAPCs can be determined according to the gene expression profile within a population. Dosages can be readily adjusted by those skilled in the art (e.g., a decrease in purity may require an increase in dosage).

Other stem cells for use according to methods of the invention are stem cells that can give rise to cell lineages derived from all three germ layers, such cells include but not limited to those described herein. As with MAPCs, other stem cells useful in the invention preferably comprise a population of cells that have about 50-55%, 55-60%, 60-65% and 65-70% purity. More preferably the purity is about 70-75%, 75-80%, 80-85%; and most preferably the purity is about 85-90%, 90-95%, and 95-100%.

U.S. Pat. No. 6,090,625 and U.S. Patent Application No. 20030166272 disclose an undifferentiated cell that is stated to be pluripotent.

U.S. Pat. No. 5,827,735 discloses mesenchymal stem cells that are stated to be pluripotent. The mesenchymal stem cells can form fibroblastic cells as well as multinucleated structures that spontaneously contract when induced to differentiate.

An embryonic-like stem cell derived from non-embryonic or postnatal animal cells or tissues, and stated to be a pluripotent (e.g., can give rise to cells of endodermal, ectodermal and mesodermal lineages), capable of self-renewal and differentiation into cells of endodermal, ectodermal and mesodermal lineages is disclosed in U.S. Patent Application No. 20030161817.

U.S. Pat. Nos. 6,200,806 and 5,843,780 refer to primate, including human, embryonic stein cells that are stated to proliferate in an in vitro culture for over one year, maintain a karyotype in which the chromosomes are euploid and not altered through prolonged culture, maintain the potential to differentiate to derivatives of endoderm, mesoderm, and ectoderm tissues throughout the culture, and are inhibited from differentiation when cultured on a fibroblast feeder layer.

U.S. Patent Applications Nos. 20010024825 and 20030008392 disclose human embryonic stem cells that are stated to proliferate in an in vitro culture for over one year, maintain a karyotype in which all the chromosomes characteristic of the human species are present and not altered through prolonged culture, maintain the potential to differentiate to derivatives of endoderm, mesoderm, and ectoderm tissues throughout the culture, and are inhibited from differentiation when cultured on a fibroblast feeder layer.

U.S. Patent Application No. 20030113910 discloses pluripotent non-embryonic stem cells, which are stated to be capable of proliferating in an in vitro culture for more than one year; maintain a karyotype in which the cells are euploid and are not altered through culture; maintain the potential to differentiate into cell types derived from the endoderm, mesoderm and ectoderm lineages throughout the culture, and are inhibited from differentiation when cultured on fibroblast feeder layers.

U.S. Patent Application No. 20030073234 discloses a clonal human embryonic stem cell line stated to be capable of sustaining a normal embryonic stem cell phenotype following at least eight months of in vitro culturing.

U.S. Pat. No. 5,914,268 discloses a pluripotent cell population that is stated to be pluripotent for development into hematopoietic cells, progenitors and progeny thereof. The pluripotent cell population is derived by culturing an embryonic stem cell population to obtain an embryoid body cell population, which is then followed by culturing said embryoid body cell population under conditions effective to produce said pluripotent cell population. The culturing conditions comprise an embryonic blast cell medium.

U.S. Patent Application No. 20030157078 refers to an isolated pluripotent pre-mesenchymal, pre-hematopoietic progenitor stem cell. Such cells are stated to have the potential to differentiate into both mesenchymal and hematopoietic phenotypes, as determined by a proliferative response to inductive growth factors and cytokines, and by their morphologic and cytochemical features.

U.S. Patent Application No. 20030161817 refers to cultured isolates comprising stem cells isolated from an umbilical cord matrix source of stem cells, other than cord blood, the isolate comprising totipotent immortal stem cells. These cell isolates are stated to be capable of proliferation in an in vitro culture for over one year, can maintain a karyotype in which all the chromosomes characteristic of the human are present and not noticeably altered through prolonged culture; and maintain the potential to differentiate into derivatives of endoderm, mesoderm or ectoderm tissues throughout the culture.

U.S. Patent Application No. 20030180269 discloses a composition that comprises stem or progenitor cells from post-partum placenta and umbilical cord blood supplemented with a plurality of embryonic-like stem cells. These cells are stated to be act-4$^+$ ABC-p$^+$, SSEA3$^-$ and SSEA4$^-$. Similarly, U.S. Patent Application No. 20030032179 discloses isolated post-partum placenta and cells isolated therefrom, which are stated to exhibit the following phenotype: CD10+, CD29$^+$, CD34$^-$, CD44$^+$, CD45, CD54$^+$, CD90$^+$, SH2$^+$, SH3$^+$, SH4$^+$, SSEA3$^-$, SSEA4$^-$, OCT-4$^+$ and ABC-p$^+$.

U.S. Patent Application Nos. 20020168763 and 20030027331 disclose homozygous stem cells. It is stated that these stem cells are produced from a mitotically activated homozygous post-meiosis I diploid germ cell by fusing two oocytes or two spermatids, preventing the extrusion of the second polar body during oogenesis, allowing the extrusion of the second polar body and spontaneous self-replication under appropriate conditions, or transferring two sperm or two haploid egg nuclei into an enucleated oocyte. This is followed by culturing said activated homozygous post-meiosis I diploid germ cell to form a blastocyst-like mass and isolating homozygous stem cells from the inner cell mass of said blastocyst-like mass.

U.S. Patent Application No. 20020090722 disclose a pluripotent cell population, stated to be derived from the method of preparing cytoplast fragments from a mammalian oocyte or fertilized zygote (the cytoplast donor), fusion of a cytoplast fragment with a cell or karyoplast (the nuclear donor) which can be taken from any mammalian species.

U.S. Patent Application No. 20020142457 discloses a cell which has been isolated from a living tissue or umbilical blood, and which is stated to be more primitive than hematopoietic or mesenchymal stem cells and to differentiate into all of the three germ layers including the ectoderm, mesoderm and endoderm.

An undifferentiated human embryonic stem cell is disclosed in U.S. Patent Application No. 20020160509. The cell is stated to be immunoreactive with markers for human pluripotent stem cells including SSEA-4, GCTM-2 antigen, and TRA 1-60, and also expresses Oct-4.

U.S. Patent Application No. 20020164794 describes an unrestricted somatic stem cell (USSC) derived from human umbilical cord blood, placental blood and/or blood samples from newborns. This somatic stem cell is stated to be distinct from but capable of differentiating into mesenchymal stem or progenitor cells, hematopoietic lineage stem or progenitor cells, neural stem or progenitor cells or endothelial stem or progenitor cells.

An isolated population of non-mouse embryonic stem cells are disclosed in U.S. Patent Application No. 20020188963. These target ES cells are stated to be obtained by co-culturing cells derived from a target embryo with non-target ES cells, such as mouse ES cells.

U.S. Patent Application No. 20030219866 discloses dedifferentiated stem cells, or what is stated to be a "stem cell-like cell."

U.S. Patent Application No. 20030219898 discloses mammalian multipotent stem cells (MSCs). These cells can be derived by methods of making more developmentally potent cells from less developmentally potent cells.

U.S. Patent Application No. 20030124720 discloses what are stated to be pluripotent and germ line competent mammalian stem cells.

U.S. Patent Application No. 20030082803 discloses what are stated to be a pluripotent or pluripotent-related cells from a mammal, which can be a human, which are produced by modulating activity or expression levels of kinases that alter the cell cycle, such as Cdk2.

U.S. Patent Application No. 20020081724 describes what are stated to be embryonic stem cell derived cell cultures, isolated by disaggregation of embryonic stem cells and embryoid bodies (EBs).

U.S. Patent Application Nos. 20020081724 and 20020137204 disclose what is stated to be a composition comprising proliferating primate pluripotent stem (pPS) cells, which is essentially free of feeder cells.

U.S. Patent Application No. 20030032177 discloses what are stated to be pluripotent or pluripotent-related cells obtained by a method of regulating differentiation potential by manipulating the expression and/or activity of a cell differentiation regulatory molecule in a pluripotent or pluripotent-related cell.

U.S. Patent Application No. 20030087431 discloses what is stated to be a stem cell line isolated from composite blastocysts (CBs) that comprise cells derived from non-viable pre-embryos. CBs are produced by: a) dissociation of non-viable pre-embryos into non-nucleated and individual nucleated cells or groups of cells; b) isolation of individual mononucleated cells or groups of mononucleated cells from disaggregated non-viable pre-embryos; c) aggregation of isolated mononucleated cells or groups of mononucleated cells from non-viable pre-embryos in a host zona pellucida; and d) culturing of the zona-encapsulated cell aggregates to allow multiplication and differentiation of cells.

Applicants herein specifically incorporate by reference all documents described above for their description of the isolation, characterization and preparation of stem cells.

According to the methods of the invention, lysosomal enzymes of interest can be produced by normal gene expression in stem cells of the invention. In addition, stem cells of the invention can be genetically altered, so that they comprise additional copies of one or more genes encoding lysosomal enzymes of interest, or over-express the endogenous gene. A genetically altered stem cell may contain DNA encoding an enzyme, under the control of a promoter that directs strong expression of the recombinant protein. Alternatively, the cell may express a gene that can be regulated by an inducible promoter or other control mechanism where conditions necessitate highly controlled regulation or timing of the expression of an enzyme.

Stem cells of the invention may be provided in their unmodified form or may be genetically engineered to express one or more genes that can provide the therapeutic effect.

For example, stem cells of the invention can contain heterologous DNA encoding a lysosomal enzyme such as β-galactosidase, hexosaminidase A, hexosaminidase B, arylsulfatase A, galactosylceramidase, α-galactosidase A, β-glucosidase, sphingomyelinase, ceramidase, acid lipase, multiple sulfatases deficiency, α-L-iduronidase, iduronate-2-sulfate sulfatase, heparan sulfaminidase, N-acetyl-α-glucosaminidase, α-glucosaminide-N-acetyltransferase, N-acetylglucosamine-6-sulfate sulfatase, N-acetylgalactosamine-6-sulfate sulfatase, β-glucuronidase, hyaluronidase, cathepsin K. N-acetyl-β-glucosaminidase, α-fucosidase, α-mannosidase, mannosidase, α-N-acetylgalactosaminidase, α-neuraminidase, cathepsin A, N-acetylglucosamine-1-phosphotransferase, α-1,4-glucosidase, palmitoyl protein thioesterase, tripeptidyl peptidase I, among others. Selection of a particular enzyme will depend on the specific type of lysosomal storage disorder to be treated.

Stem cells of the invention can be genetically modified to contain heterologous DNA (preferably encoding a lysosomal enzyme) by introducing isolated heterologous DNA or RNA into the cell by a variety of methods known to those of skill in the art. These methods are generally grouped into four major categories: (1) viral transfer, including the use of DNA or RNA viral vectors, such as retroviruses (including lentiviruses), Simian virus 40 (SV40), adenovirus, Sindbis virus, and bovine papillomavirus, for example; (2) chemical transfer, including calcium phosphate transfection and DEAE dextran transfection methods; (3) membrane fusion transfer, using DNA-loaded membranous vesicles such as liposomes, red blood cell ghosts, and protoplasts, for example; and (4) physical transfer techniques, such as microinjection, electroporation, or direct "naked" DNA transfer.

Stem cells of the invention can be genetically altered by insertion of pre-selected isolated DNA, by substitution or augmentation of a segment of the cellular genome with pre-selected isolated DNA, or can be altered by deletion of or inactivation of at least a portion of the cellular genome of the cell. Deletion or inactivation of at least a portion of the cellular genome can be accomplished by a variety of means, including but not limited to homologous recombination. In general, "homologous recombination" is the substitution of a segment of DNA by another that is identical or nearly so. Thus, to homologously recombine an exogenous DNA molecule is to physically exchange segments of the molecule, preferably segments flanking a desired nucleotide sequence for insertion, with homologous genomic DNA sequences of the stem cell, such that the exogenous DNA molecule, or a portion thereof, is inserted into the stem cell genome. For a review of homologous recombination, see Lewin, B., *Genes V*, Oxford University Press, New York, 1994, pp. 968-997; and Capecchi, M., (1989) Science 244:1288-1292; Capecchi, M., (1989) *Trends Genet*. 5(3): 70-76. See also, U.S. Pat. Nos. 5,783,385, 5,733,761, and 5,641,670, the contents of which are specifically incorporated by reference for their entire disclosure relating to methods of homologous recombination. Methods of non-homologous recombination are also known, for example, as described in U.S. Pat. Nos. 6,623,958, 6,602,686, 6,541,221, 6,524,824, 6,524,818, 6,410,266, 6,361,972, the contents of which are specifically incorporated by reference for their entire disclosure relating to methods of non-homologous recombination.

The altered genome may contain the genetic sequence of a screenable or selectable marker gene that is expressed so that the progenitor cell with an altered genome, or its progeny, can be differentiated from progenitor cells having an unaltered genome. For example, the marker may be a green, red, yellow fluorescent protein, β-galactosidase, the neomycin resistance gene, dihydrofolate reductase (DHFR), or hygromycin phosphotransferase, but are not limited to these examples.

Insertion of one or more pre-selected DNA sequences can be accomplished by homologous recombination or by viral integration into the host cell genome. The desired gene sequence can also be incorporated into the cell, particularly into its nucleus, using a plasmid expression vector and a nuclear localization sequence. Methods for directing polynucleotides to the nucleus have been described in the art. The genetic material can be introduced using promoters that will allow for the gene of interest to be positively or negatively induced using certain chemicals/drugs, to be eliminated following administration of a given drug/chemical, or can be tagged to allow induction by chemicals (including but not limited to the tamoxifen responsive mutated estrogen receptor) expression in specific cell compartments (including but not limited to the cell membrane).

Calcium phosphate transfection can be used to introduce plasmid DNA containing a target gene or polynucleotide into isolated or cultured multipotent stem cells and is a standard method of DNA transfer to those of skill in the art. DEAE-dextran transfection, which is also known to those of skill in the art, may be preferred over calcium phosphate transfection where transient transfection is desired, as it is often more efficient. Since the cells of the present invention are isolated cells, microinjection can be particularly effective for transferring genetic material into the cells. This method is advantageous because it provides delivery of the desired genetic material directly to the nucleus, avoiding both cytoplasmic and lysosomal degradation of the injected polynucleotide. This technique has been used effectively to accomplish germline modification in transgenic animals. Stem cells of the present invention can also be genetically modified using electroporation or nucleofection.

Liposomal delivery of DNA or RNA to genetically modify the cells can be performed using cationic liposomes, which form a stable complex with the polynucleotide. For stabilization of the liposome complex, dioleoyl phosphatidylethanolamine (DOPE) or dioleoyl phosphatidylcholine (DOPQ) can be added. Commercially available reagents for liposomal transfer include LipofectinS (Life Technologies). Lipofectin, for example, is a mixture of the cationic lipid N-[1-(2,3-dioleyloyx)propyl]-N—N—N— trimethyl ammonia chloride and DOPE. Liposomes can carry larger pieces of DNA, can generally protect the polynucleotide from degradation, and can be targeted to specific cells or tissues. The efficiency of cationic lipid-mediated gene transfer can be enhanced by incorporating purified viral or cellular envelope components, such as the purified G glycoprotein of the vesicular stomatitis virus envelope (VSV-G). Gene transfer techniques that have been shown effective for delivery of DNA into primary and established mammalian cell lines using lipopolyamine-coated DNA can be used to introduce target DNA into stem cells of the invention.

Naked plasmid DNA can be injected directly into a tissue mass formed of differentiated cells from stem cells of the invention. This technique has been shown to be effective in transferring plasmid DNA to skeletal muscle tissue, where expression in mouse skeletal muscle has been observed for more than 19 months following a single intramuscular injection. More rapidly dividing cells take up naked plasmid DNA more efficiently. Therefore, it is advantageous to stimulate cell division prior to treatment with plasmid DNA. Microprojectile gene transfer can also be used to transfer genes into stem cells of the invention either in vitro or in vivo. The basic procedure for microprojectile gene transfer was described by J. Wolff in Gene Therapeutics (1994), page 195. Similarly, microparticle injection techniques have been described previously, and methods are known to those of skill in the art. Signal peptides can be also attached to plasmid. DNA to direct the DNA to the nucleus for more efficient expression.

Viral vectors are used to genetically alter stem cells of the invention and their progeny. Viral, vectors are used, as are the physical methods previously described, to deliver one or more nucleic acids such as target genes, polynucleotides, antisense molecules, or ribozyme sequences into the cells. Viral vectors and methods for using them to deliver DNA to cells are well known to those of skill in the art. Examples of viral vectors that can be used to genetically alter the cells of the present invention include, but are not limited to, adenoviral vectors, adena-associated viral vectors, retroviral vectors (including lentiviral vectors), alphaviral vectors (e.g., Sindbis vectors), and herpes virus vectors.

iv. Administration of Stem Cells

Stem cells of the invention or their progeny can be administered via localized injection, including by catheter administration, systemic injection, intraperitoneal injection, intracranial injection, intramuscular, intrahepatic, parenteral administration, intraarterial injection, injection into the lateral cerebral ventricles or intraplacental injection. For example, MAPCs can be administered to a subject by a variety of methods known in the art. Preferably, administration is through injection, including but not limited to surgical intramyocardial injection, transendocardial injection, intracoronary injection, transvascular injection, intramuscular injection and/or intravenous injection. Injection can be directed into any desired organ system, such as directly into the bone marrow, liver, cardiac tissue or the vessels thereof. Stem cells of the invention can be administered in the form of a tissue-engineered structure, such as a matrix-based composition or a bioartificial organ, such as a liver or kidney assist device.

Intravenous injection is the simplest method of cell administration, however a greater degree of dependence on homing of the stem cells is required for them to reach the tissue of interest (e.g., myocardium). Carefully controlled dosing, which is readily determined by one skilled in the art, enhances this method of administration.

Certain cytokines can alter or affect the migration of MAPCs or their differentiated counterparts to the site of damaged muscle tissue. "Homing" of stem cells to the injured muscle tissue is essential, as it concentrates the implanted cells in an environment favorable to their growth and function. In more acute situations, the stem cells can be administered either peripherally or locally through the circulatory system. When the homing signals may be less intense, injection of the cells directly into the site may produce a more favorable outcome. Pretreatment of a patient with cytokine(s) to promote homing is another alternative contemplated in the methods of the present invention. Additionally, exogenous factors (e.g., cytokines, differentiation factors and anti-apoptosis factors) can be administered prior to, after or concomitantly with MAPCs. For example, a form of concomitant administration would comprise combining a factor of interest in the MAPC suspension media prior to administration. Doses for administration are variable and may include an initial administration followed by subsequent administrations.

The skilled artisan can readily determine the amount of cells and optional additives, vehicles, and/or carrier in compositions and to be administered in methods of the invention. Typically, any additives (in addition to the active stem cell(s) and/or cytokine(s)) are present in an amount of 0.001 to 50 wt % solution in phosphate buffered saline, and the active ingredient is present in the order of micrograms to milligrams, such as about 0.0001 to about 5 wt %, preferably about 0.0001 to about 1 wt %, most preferably about 0.0001 to about 0.05 wt % or about 0.001 to about 20 wt %, preferably about 0.01 to about 10 wt %, and most preferably about 0.05 to about 5 wt %. Of course, for any composition to be administered to an animal or human, and for any particular method of administration, it is preferred to determine therefore: toxicity, such as by determining the lethal dose (LD) and $LD_{50}$ in a suitable animal model e.g., rodent such as mouse; and, the dosage of the composition(s), concentration of components therein and timing of administering the composition(s), which elicit a suitable response. Such determinations do not require undue experimentation from the knowledge of the skilled artisan, this disclosure and the documents cited herein. And, the time for sequential administrations can be ascertained without undue experimentation.

When administering a therapeutic composition of the present invention, it will generally be formulated in a unit dosage injectable form (solution, suspension, emulsion). The pharmaceutical formulations suitable for injection include sterile aqueous solutions and dispersions. The carrier can be a solvent or dispersing medium containing, for example, water, saline, phosphate buffered saline, polyol (for example, glycerol, propylene glycol, liquid polyethylene glycol, and the like) and suitable mixtures thereof.

Additionally, various additives which enhance the stability, sterility, and isotonicity of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin. According to the present invention, however, any vehicle, diluent, or additive used would have to be compatible with the cells.

Sterile injectable solutions can be prepared by incorporating the cells utilized in practicing the present invention in the required amount of the appropriate solvent with various amounts of the other ingredients, as desired.

In one embodiment, stem cells of the invention can be administered initially, and thereafter maintained by further administration. For instance, stem cells of the invention can be administered by one method of injection, and thereafter further administered by a different or the same type of method. Preferably, stem cells of the invention can be administered by intraperitoneal injection until the enzyme reaches a suitable level. The patient's enzyme levels can then be maintained, for example, by intravenous injection, although other forms of administration, dependent upon the patient's condition, can be used. Stem cells of the invention or their progeny can be administered via localized injection, including catheter administration, systemic injection, intracranial injection, intraarterial injection, parenteral administration, injection into the lateral cerebral ventricles, intraplacental, or intrauterine injection into an embryo.

Stem cells of the invention can be administered in the form of a tissue-engineered structure, such as a matrix-based composition. A method to potentially increase cell survival when introducing the cells into a subject in need thereof is to incorporate stem cells of the invention or their differentiated progeny of interest into a biopolymer or synthetic polymer matrix. Depending on the subject's condition, the site of injection might prove inhospitable for cell seeding and growth because of scarring or other impediments. Examples of biopolymer include, but are not limited to, cells mixed with fibronectin, fibrin, fibrinogen, thrombin, collagen, and proteoglycans. This could be constructed with or without included cytokines or differentiation factors. Additionally, these could be in suspension, but residence time at sites subjected to flow would be nominal. Another alternative is a three-dimensional gel with cells entrapped within the interstices of the cell biopolymer admixture. Again, differentiation factors or cytokines could be included within the cells. These could be deployed by injection via various routes described herein.

An issue concerning the therapeutic use of stem cells of the invention is the quantity of cells necessary to achieve an optimal effect. In current human studies of autologous mononuclear bone marrow cells, empirical doses ranging from 1 to $4 \times 10^7$ cells have been used with encouraging results. However, different scenarios may require optimization of the amount of cells injected into a tissue of interest. Thus, the quantity of cells to be administered will vary for the subject being treated. In a preferred embodiment, between $10^4$ to $10^8$, more preferably $10^5$ to $10^7$, and most preferably, $3 \times 10^7$ stem cells of the invention and optionally, 50 to 500 µg/kg per day of a cytokine can be administered to a human subject. However, the precise determination of what would be considered an effective dose may be based on factors individual to each subject, including their size, age, target organ, and amount of time since the unwanted accumulation of substrate began. Therefore, dosages can be readily ascertained by those skilled in the art from this disclosure and the knowledge in the art.

It is noted that human subjects are treated generally longer than the mice or other experimental animals, such that treatment has a length proportional to the length of the disease process and effectiveness. The doses may be single doses or multiple doses over a period of several days. Thus, one of skill in the art can scale up from animal experiments, e.g., rats, mice, canines and the like, to humans, by techniques from this disclosure and documents cited herein and the knowledge in the art, without undue experimentation. The treatment generally has a length proportional to the length of the disease process and drug effectiveness and the subject being treated.

Examples of compositions comprising stem cells of the invention include liquid preparations for administration, including suspensions; and, preparations for injectable administration, such as sterile suspensions or emulsions. Such compositions may be in admixture with a suitable carrier, diluent, or excipient such as sterile water, physiological saline, glucose, dextrose, or the like. The compositions can also be lyophilized. The compositions can contain auxiliary substances such as wetting or emulsifying agents, pH buffering agents, gelling or viscosity enhancing additives, preservatives, flavoring agents, colors, and the like, depending upon the route of administration and the preparation desired. Standard texts, such as "REMINGTON'S PHARMACEUTICAL SCIENCE", 17th edition, 1985, incorporated herein by reference, may be consulted to prepare suitable preparations, without undue experimentation.

Compositions of the invention are conveniently provided as liquid preparations, e.g., isotonic aqueous solutions, suspensions, emulsions or viscous compositions, which may be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues.

The choice of suitable carriers and other additives will depend on the exact route of administration and the nature of the particular dosage form, e.g., liquid dosage form (e.g., whether the composition is to be formulated into a solution, a suspension, gel or another liquid form, such as a time release form or liquid-filled form).

Solutions, suspensions and gels may contain a large amount of water (preferably purified, sterilized water) in addition to the cells. Minor amounts of other ingredients such as pH adjusters (e.g., a base such as NaOH), emulsifiers or dispersing agents, buffering agents, preservatives, wetting agents and jelling agents (e.g., methylcellulose), may also be present. The compositions can be isotonic, i.e., they can have the same osmotic pressure as blood and lacrimal fluid.

The desired isotonicity of the compositions of this invention may be accomplished using sodium chloride, or other pharmaceutically acceptable agents such as dextrose, boric acid, sodium tartrate, propylene glycol or other inorganic or organic solutes. Sodium chloride is preferred particularly for buffers containing sodium ions.

Viscosity of the compositions, if desired, can be maintained at the selected level using a pharmaceutically acceptable thickening agent. Methylcellulose is preferred because it is readily and economically available and is easy to work with. Other suitable thickening agents include, for example, xanthan gum, carboxymethyl cellulose, hydroxypropyl cellulose, carbomer, and the like. The preferred concentration of the thickener will depend upon the agent selected and an amount of the thickener is used so as to achieve the selected viscosity. Viscous compositions can be prepared from solutions by the addition of such thickening agents.

A pharmaceutically acceptable preservative or cell stabilizer can be employed to increase the life of the compositions. Preferably, if preservatives are necessary, it is well within the purview of the skilled artisan to select compositions that will not affect the viability or efficacy of stem cells of the invention as described in the present invention.

Those skilled in the art will recognize that the components of the compositions should be selected to be chemically inert. This will present no problem to those skilled in chemical and pharmaceutical principles, or problems can be readily avoided by reference to standard texts or by simple experiments (not involving undue experimentation), from this disclosure and the documents cited herein.

Compositions can be administered in dosages and by techniques well known to those skilled in the medical and veterinary arts taking into consideration such factors as the age, sex, weight, and condition of the particular patient, and the composition form used for administration (e.g., solid vs. liquid). Dosages for humans or other mammals can be determined without undue experimentation by the skilled artisan, from this disclosure, the documents cited herein, and the knowledge in the art.

Suitable regimen for initial administration and further doses or for sequential administrations also are variable, may include an initial administration followed by subsequent administrations; but nonetheless, can be ascertained by the skilled artisan, from this disclosure, the documents cited herein, and the knowledge in the art.

v. Administration of Stem Cells to a Subject in Utero

In a preferred embodiment, the invention is directed to a method for providing a lysosomal enzyme to a subject in utero by administering stem cells of the invention.

Administration of stem cells of the invention to a subject in utero can be performed by direct injection into the umbilical vein or liver of the fetus, intraperitoneal injection, intraplacental injection, or intrauterine injection into an embryo. Preferably, stem cells of the invention are administered via intraperitoneal injection(s) beginning in the two trimesters. Preferably, intraperitoneal injection(s) begin in the first trimester.

In a preferred embodiment, infants are treated by methods of the invention. Treatment can be by administration of stem cells of the invention to the infant postpartum, or when in utero.

Successful perinatal transfer of stem cells of the invention can be performed and assessed by direct visualization of cells, either by hysterotomy or other methods, or if cells are transduced with a marker that allows for easy detection of donor cells. Perinatal transfer can also be used in combination with ultrasound guidance (Surbek, D. V., et al., (2002) *Am. J. Obstet. Gynecol.* 187: 960-3). While the maternal and fetal cells do cross placenta, most are thought to be cleared by the placenta. Thus, non-maternal infusion is preferred.

In utero infusions in humans and large mammals (goat, sheep) are most preferably performed in the first trimester. In utero transplantation is known in the art and the techniques are incorporated by reference (Carrier, E., et al, (1997) *Transplantation* 64(4): 627-633; Carrier, E., et al, (1995) *Blood* 86(12): 4681-4690). Stem cells of the invention can also be administered earlier in development, and this can result in greater engraftment and correction of prenatal birth defects associated with the lysosomal storage diseases disclosed herein.

Stem cells of the invention are readily detectable in fetal blood during the first and second trimesters. Thus, stem cell infusion can occur during development of each organ system, wherein the timing of injections can correspond to periods specific for each organ system. Since the cells may not establish "pools", their differentiated progeny, or other stem cell precursors, available when needed at later times (i.e., at times of injury), optimal administration may require multiple stem cell infusions, both pre- and post-natal.

vi. Differentiation of MAPCs

According to methods of the invention, either MAPCs, or the differentiated progeny thereof, can be administered to provide lysosomal enzymes. MAPCs can be provided and differentiated in vivo, or differentiated ex vivo prior to administration.

MAPCs of the invention can be induced to form at feast one differentiated cell type of mesodermal, ectodermal and endodermal origin. For example, the MAPCs have the capacity to be induced to differentiate to form at least osteoblast, chondrocyte, cartilage, adipocyte, fibroblast, marrow stroma, skeletal muscle, smooth muscle, cardiac muscle, endothelial, epithelial, endocrine, exocrine, hematopoietic, glial, neuronal, oligodendrocyte, skin, liver, pancreatic, islet, gut, or kidney cell types.

Thus, methods of the invention also provide for administration of differentiated progeny of MAPCs, wherein the progeny cell may comprise bone, cartilage, adipocyte, fibroblast, marrow, stroma, skeletal muscle, smooth muscle, cardiac muscle, endothelial, epithelial, endocrine, exocrine, hematopoietic, glial. neuronal, oligodendrocyte, skin, liver, pancreatic, islet, gut, or kidney cells, or an epidermal associated structure (such as a hair follicle). Differentiated progeny derived from the MAPCs described herein can be directly administered to a particular organ or organ system that is deficient or comprises decreased lysosomal enzyme activity.

MAPCs can be induced to differentiate to form committed progenitors and tissue-specific cell types using appropriate growth or differentiation factors, chemokines, and cytokines. MAPCs can be differentiated in vivo or ex vivo. MAPCs, or differentiated progeny thereof, can be co-administered in the presence of cytokines and growth/differentiation factors to promote differentiation to a preferred cell type. This can be advantageous if, for example, engraftment of a particular organ or organ system is desired. Cells can be differentiated in culture or co-infused with cytokines and differentiation factors according to the developmental progression of the organs or organ systems in the fetus.

To form osteoblasts, confluent MAPCs can be cultured with about $10^{-6}$-$10^{-8}$M (preferably about $10^{-7}$M) dexamethasone, β-glycerophosphate and 5-20 mM (preferably. 10 mM) ascorbic acid. The presence of osteoblasts can be detected using Von Kossa staining (silver reduction of $CaPO_4$), or antibodies against bone sialoprotein, osteonectin, osteopontin and osteocalcin (detectable by immunohistochemistry or Western Blotting). After 14-21 days of culture, >80% of cells stain positive with these antibodies.

To achieve differentiation into chondroblasts, MAPCs can be trypsinized, and cultured in serum-free DMEM supplemented with 50-100 ng/mL (preferably 100 ng/mL) of TGF-β1 in micromass suspension culture. Small aggregates of cartilage can be detected in the bottom of the tubes that stain positive with toluidine blue. Collagen type I can be detected initially throughout the micromass (day 5), but after about 14 days, it can only be detected in the outer layer of fibrillar cartilage. Collagen type II becomes detectable after about 5 days and strongly stains the micromass by about day 14. Staining for bone sialoprotein was negative or minimally positive in the outer fibrinous cartilage layer. Variable staining can be visualized for osteonectin, osteocalcin and osteopontin. The presence of collagen type II can be confirmed by Western blot and RT-PCR. In addition, RT-PCR on cells recovered after 5 days can show the presence of the cartilage specific transcription factors CART1 and CD-RAP1.

To induce adipocyte differentiation, about $10^{-7}$ to about $10^{-6}$ M (preferably about $10^{-7}$M) dexamethasone, about 50 to about 200 µg/ml (preferably about 100 µg/ml) insulin or media supplemented with approximately 20% horse serum can be used. Adipocyte differentiation can be detected by examination with light microscopy, staining with oil-red, or detection of lipoprotein lipase (LPL), adipocyte lipid-binding protein (aP2), or peroxisome proliferator-activated receptor gamma (PPAR). Methods for detection of cellular markers and products are known to those of skill in the art, and can include detection using specific ligands, such as, for example, troglitazone (TRO) and rosiglitazone (RSG), which bind to PPARγ.

To induce skeletal muscle cell differentiation, confluent MAPCs can be treated with about 1 to about 3 µM (preferably about 3 µM) of 5-azacytidine in MAPC expansion medium for 24 hours. Cultures can then be maintained in MAPC medium disclosed above. Differentiation can be evaluated by Western blot and immunohistochemistry. Skeletal muscle differentiation in vitro can be demonstrated by detecting sequential expression of Myf-5, Myo-D, Myf-6, myogenin, desmin, skeletal actin and skeletal myosin, either by immunohistochemistry or Western blot analysis using standard techniques known to those of skill in the art and commercially available antibodies. Five days after induction with 5-azacytidine, the Myf5, Myo-D and Myf-6 transcription factors can be detected in approximately 50% of cells. After 14-18 days, Myo-D is expressed at significantly lower levels, whereas Myf5 and Myf6 persisted. Desmin and skeletal actin can be detected as early as four days after induction, and skeletal myosin at about 14 days. By immunohistochemistry, 70-80% of cells express mature muscle proteins after about 14 days. Treatment with 5-azacytidine resulted in expression of Gata4 and Gata6 during the first week of culture. In addition, low levels of troponin-T could be detected from about day two onwards. Smooth muscle actin was detected at two days after induction and persisted for 14 days. When 20% horse serum was added, a fusion of myoblasts into myotubes that were multinucleated can be seen. Using double immunofluorescence, transduced myoblasts could fuse with differentially lateral myocytes.

Smooth muscle cells can also be induced by culturing MAPCs in serum-free medium, without growth factors, supplemented with high concentrations (about 50 to about 200 ng/ml, preferably about 100 ng/ml) of platelet-derived growth factor (PDGF). Cells should preferably be confluent at initiation of differentiation. Terminally differentiated smooth muscle cells can be identified by detecting expression of desmin, smooth muscle specific actin, and smooth muscle specific myosin by standard methods known to those of skill in the art. Smooth muscle actin can be detected from about day two onwards and smooth muscle myosin after about 14 days. Approximately 70% of cells stain positive with anti-smooth muscle actin and myosin antibodies. The presence of myogenin can be seen from day four onwards and desmin after 6 days. Myf5 and Myf6 proteins can also be detected after 2-4 days, which persist until about day 15.

Cardiac muscle differentiation can be accomplished by adding about 5 to about 200 ng/ml (preferably about 100 ng/ml) of basic fibroblast growth factor (bFGF) to the standard serum-free culture media without growth factors, as previously described. Confluent MAPCs can be exposed to 3 µM (preferably about 3 µM) 5-azacytidine and to $10^{-5}$-$10^{-7}$M (preferably $10^{-6}$M) retinoic acid, and then can be cultured in MAPC expansion medium afterwards. Alternatively, MAPCs can be cultured with either of these inducers alone or a combination of both and then cultured in serum-free medium with 50-200 ng/mL (preferably 100 ng/mL FGF2 or a combination of 5-20 ng/mL (preferably 10 ng/mL) BMP-4 and 100 ng/mL FGF2. Expression of proteins consistent with cardiomyocytes can be observed under these conditions. Gata4 and Gata6 are expressed as early as about day 2 and persisted until about day 15. Cardiac troponin-T is expressed after day 4 and cardiac troponin-1 from about day 6 on, while ANP can be detected after about day 11. These cardiac proteins were detected in >70% of cells by immuno-histochemistry on day 15. The transcription factor Myf6 can be seen from about day 2 on. Expression of desmin can begin on day 6 and myogenin on day 2. Skeletal actin was also detected. When the cultures are maintained for >3 weeks, cells can form syncytia. Infrequent spontaneous contractions occurring in the cultures can be observed, which were propagated over several mm distance.

To form endothelial cells, MAPCs are cultured serum-free in MAPC medium with 20 ng/mL VEGF. The appearance of CD34 on the cell surface can then be seen and cells express vWF by day 14. In addition, the differentiated endothelial cells express Tie, Tek, Flk1 and Flt1, PECAM, P-selectin and E-selectin, and CD36. When VEGF-induced cells are cultured on Matrigel™ or collagen type IV, vascular tube formation can be seen.

To form hematopoietic cells, MAPCs can be replated on collagen type IV in PDGF-BB- and EGF-containing MAPC medium with 5% FCS and 100 ng/mL SCF conditioned by the AFT024 feeder layer, a fetal liver derived mesenchymal cell, line that can support murine and human repopulating stem cells ex vivo. Cells recovered from these cultures express c-Kit, cMyb, Gata2 and G-CSF-R but not CD34, detectable by RT-PCR. Because hematopoiesis is induced by factors that are released by embryonal visceral endoderm, human MAPCs can be co-cultured with β-Gal+ murine EBs in the presence of human SCF, Flt3-L, Tpo and Epo. Incubating MAPCs with IL-Ia, FCS, and horse serum can induce "stromal" differentiation. To demonstrate that these cells can support hematopoiesis, feeder layers can be irradiated at 2,000 cGy and CD34+ cord blood cells plated in contact with the feeder. After 1, 2 and 5 weeks, progeny can be replated in methylcellulose assay to determine the number of colony forming cells (CFC). A 3-5-fold expansion of CFC can be seen after about 2 weeks and maintenance of CFC at about 5 weeks, similar to cultures of CD34+ cells in contact with the murine fetal liver derived feeder, AFT024.

MAPCs induced with VEGF, the hematopoietic cytokines SCF, Flt3-L, Tpo and Epo in MAPC medium containing EGF conditioned by the hematopoietic supportive feeder A-FT024 differentiated into glial fibrilar acidic protein (GFAP) positive astrocytes, galactocerebroside (GalC) positive oligodendrocytes and neurofilament positive neurons. When <50% confluent cultures of human marrow derived MAPCs cultured with EGF and PDGF-BB are switched to medium containing 50-500 ng/mL (preferably 100 ng/mL) of FGF2, differentiation to cells expressing of astrocytes, oligodendrocytes and neurons can be seen after 2-4 weeks. After two weeks in culture, cells are GFAP positive, GalC positive ad neurofilament-200 positive. After three weeks, fewer cells are GFAP or GalC positive, but cells can stain positive for β-tubulin-III, neurofilament-68, neurofilament-160, neurofilament-200, neuron specific enolase (NSE) and microtubule associated protein-2 (MAP2). GABA, parvalbumin, tyrosine hydroxylase, DOPA-decarboxylase, and tryptophan hydroxylase are not detected. The number of neurites per neuron increased from 2, 3 to 4 weeks after differentiation. Differentiation to cells with characteristics of astrocytes, oligodendrocytes and neurons can be confined by demonstrating presence of GFAP, myelin basic protein (MBP) and neurofilament-200 by Western blot and RT-PCR analysis in FGF2 treated but not undifferentiated MAPCs.

FGF-9, first isolated from a glioblastoma cell line, can induce proliferation of glial cells in culture. FGF-9 is found in vivo in neurons of the cerebral cortex, hippocampus, substantia nigra, motor nuclei of the brainstem and Purkinje cell layer. When cultured for 3 weeks with 5-50 ng/mL (preferably 10 ng/mL) FGF-9 and EGF MAPCs can generate astrocytes, oligodendrocytes and GABAergic and dopaminergic neurons. During CNS development, FGF-8, expressed at the mid/hindbrain boundary and by the rostral forebrain, in combination with Sonic hedgehog, induces differentiation of dopaminergic neurons in midbrain and forebrain. It was found that when MAPCs are cultured with 5-50 ng/mL (preferably 10 ng/mL) FGF-8 and EGF for 3 weeks, both dopaminergic and GABAergic neurons were produced. FGF-10 is found in the brain in very low amounts and its expression is restricted to the hippocampus, thalamus, midbrain and brainstem, where it is preferentially expressed in neurons, but not in glial cells. Culture of MAPCs in 5-50 ng/mL (preferably 10 ng/mL) FGF-10 and EGF for three weeks can generate astrocytes and oligodendrocytes, but not neurons. FGF-4 is expressed by the notochord and is required for the regionalization of the midbrain. When treated with 5-50 ng/mL (preferably 10 ng/mL) FGF-4 and EGF for 3 weeks, MAPCs differentiate into astrocytes and oligodendrocytes, but not neurons.

Other growth factors that are specifically expressed in the brain and that affect neural development in vivo and in vitro include brain derived neurotrophic factor (BDNF), glial derived neurotrophic factor (GDNF) and ciliary neurotrophic factor (CNTF). BDNF is a member of the nerve growth factor family that promotes in vitro differentiation of NSC, human subependymal cells, and neuronal precursors to neurons and promotes neurite outgrowth of hippocamal stem cells in vivo. Consistent with the known function of BDNF to support survival of dopaminergic neurons of the substantia nigra, when MAPCs are treated with 5-50 ng/mL (preferably 10 ng/mL) BDNF and EGF, exclusive differentiation into tyrosine hydroxylase positive neurons was seen. GDNF is a member of the TGF-superfamily. In early neurogenesis, GDNF is expressed in the anterior neuroectoderm, suggesting that it may play a key role in neuronal development. GDNF promotes survival of motor neurons in peripheral nerve and muscle and has neurotrophic and differentiation abilities. It was found that 5-50 ng/mL (preferably 10 ng/mL) GDNF can induce MAPCs to differentiate into GABAergic and dopaminergic neurons. CNTF, first isolated from ciliary ganglion, is a member of the gp130 family of cytokines. CNTF promotes neuronal survival early in development. In embryonic rat hippocampal cultures CNTF increased the numbers of GABAergic and cholinergic neurons. In addition, it prevents cell death of GABAergic neurons and promotes GABA uptake. A concentration between 5-50 ng/mL (preferably 10 ng/mL) of CNTF can exert the same GABAergic induction on. MAPCs to differentiate exclusively into GABAergic neurons after about three weeks of exposure to CNTF.

Epithelial cells can be generated by treating confluent MAPCs with 10 ng/mL hepatocyte growth factor (HGF). alone or in combination with keratinocyte growth factor (KGF). After about 14 days, large epitheloid cells can be seen that expressed the HGF receptor, cytokeratin 8, 18 and 19. The presence of cytokeratin-19 suggests possible differentiation to biliary epithelium. Changing the matrix from fibronectin to a collagen gel or Matrigel™ can improve the generation of cytokeratin-18 expressing cells with morphology of epithelial cells.

Other stem cells of the invention can be differentiated according to methods well-known in the art. For example, differentiation can proceed according to the methods disclosed in U.S. Pat. Nos. 5,333,727 and 6,015,671, specifically incorporated by reference for the differentiation methods described therein. In addition, it is well within the skill of one in the art to adjust the parameters of the methods described above to suit stem cells of the invention other than MAPCs.

Methods of identifying and subsequently separating differentiated cells from their undifferentiated counterparts can be carried out by methods well known in the art. Cells that have been induced to differentiate can be identified by selectively culturing cells under conditions whereby differentiated cells outnumber undifferentiated cells. Similarly, differentiated cells can be identified by morphological changes and characteristics that are not present on their undifferentiated counterparts, such as cell size, the number of cellular processes (i.e. formation of dendrites and/or branches), and the complexity of intracellular organelle distribution. Also contemplated are methods of identifying differentiated cells by their expression of specific cell-surface markers such as cellular receptors and transmembrane proteins. Monoclonal antibodies against these cell-surface markers can be used to identify differentiated cells. Detection of these cells can be achieved through fluorescence activated cell sorting (FACS), immunohistochemistry, immunofluorescence, and enzyme-linked immunosorbent assay (ELISA). From the standpoint of transcriptional upregulation of specific genes, differentiated cells often display levels of gene expression that are different from undifferentiated cells. Reverse-transcription polymerase chain reaction (RT-PCR) can also be used to monitor changes in gene expression in response to differentiation. Similarly, techniques such as in situ hybridization and fluorescence in situ hybridization can be used to detect mRNA levels in specific cells or tissues. In addition, whole genome analysis using microarray technology and proteomic arrays can be used to identify differentiated cells.

Accordingly, once differentiated cells are identified, they can be separated from their undifferentiated counterparts, if necessary. The methods of identification detailed above also provide methods of separation, such as FACS, preferential cell culture methods, ELISA, magnetic beads, and combinations thereof. FACS can be used to identify and separate cells based on cell-surface antigen expression.

The following examples are put forth so as to provide those of ordinary skill in the art with a complete disclosure and description of how to make and use the cells of the invention, and are not intended to limit the scope of what the inventors regard as their invention.

EXAMPLES

Example 1: MAPC Engraftment in Severe Combined Immunodeficiency (SCID), Recipients MAPCs were isolated from bone marrow of C57BL/6J-rosa26 mice, which contain the lacZ reporter gene and the neomycin resistance gene. These mononuclear bone marrow cells are capable of differentiating into endodermal, mesodermal, and ectodermal germ layers. Bone marrow mononuclear cells (n=2, age 8 weeks) were depleted of CD45 and GlyA positive cells using micromagnetic beads (Miltenyi Biotec, Sunnyvale, Calif.). CD4Y$^-$, GlyA$^-$ cells were plated in medium consisting of 60% DMEM-LG (Gibco-BRL, Grand Island, N.Y.), 40% MCDB-201 (Sigma Chemical Co., St. Louis, Mo.), with 1× insulin-transferrin-selenium (ITS), IX linoleic acid-bovine serum albumin (LA-ESA), $10^{-9}$ M dexamethasone (Sigma) and $10^{-4}$ M ascorbic acid-2-phosphate (Sigma), 100 U penicillin and 1000 U streptomycin (Gibco) on fibronectin (FN; Sigma), laminin, collagen type IV, and Matrigel™ with 2% fetal calf serum (FCS; Hyclone Laboratories, Logan, Utah) and additionally supplemented with 1-25 ng/ml each of epidermal growth factor (EGF), platelet derived growth factor-BE (PDGF-BB) and leukemia inhibitory factor (LIF; all from R&D Systems, Minneapolis, Minn.). After three weeks of culture, remaining $CD4Y^-$/$GlyA^-$ cells were selected, subcultured at 10 cells/well, and maintained between 0.5 to $1.5 \times 10^3$ cells/cm². MAPCs cultured on FN with 10 ng/ml EGF, 10 ng/ml PDGF-BB and 10 ng/ml LIF were CD3, Gr-1, Mac-1, CD19, CD34, CD44, CD45, c-Kit, and major histocompatibility complex (MHC) class I and II-negative, expressed low levels of Flk1 and Sca1, and higher levels of CD13 and SSEA-1.

MAPCs were injected into embryonic day 15/16 fetal BALB/c-SCID mice, or newborn BALB/c-SCID mice ranging in age from 0-5 days. Mice were sacrificed at 10, 20, and 30 weeks post-transfer of MAPCs and tissues were tested for engraftment by immunohistochemistry and quantitative PCR. Under general anesthesia, a midline abdominal incision was performed and the uterus of pregnant BALB/c-SCID mice (E15/16 and E16/17) was exposed. After direct visualization of individual fetuses, $1 \times 10^6$ of C57BL/6J-rosa26 MAPCs (in 5-10 µl of PBS) were slowly injected into the fetal liver parenchyma across chorionic membrane and uterine wall.

Tissue specimens of the recipient animals were cryopreserved in OCT at $-80°$ C. Fresh frozen sections of approximately 6 µm thick were mounted on glass slides, fixed in acetone for 10 minutes at room temperature and incubated in isotype sera for 20 minutes. Cryosections were stained for β-galactosidase (fluorescein isothiocyanate (FITC)-coupled anti-β-galactosidase antibody, Rockland Immunochemicals) to assess exact histological location of the C57BL/6J-rosa26 MAPC-derived cells in the recipients. Tissues were also examined for the tissue-specific characteristics of the C57BL/6J-rosa26 MAPC-derived cells by dual color immunofluorescence, using FITC-coupled anti-β-galactosidase antibody along with an antibody for one of the following tissue specific antigens. Pan-cytokeratin stained for pulmonic and colonic epithelium as well as spleen and skin, albumin and cytokeratin-18 for liver, anti-mouse IgG Cy3 conjugate (all from Sigma), and nuclear counter stain (TO-PRO-3, Molecular Probes). Between steps, slides were washed in PBS. Slides were examined by confocal fluorescence microscopy (Olympus AX70, Olympus optical Co. LTD, Japan). Z-stack series in 3D reconstruction of confocal images were used to distinguish true positive cells from a simple overlay of two separate cells.

MAPCs engrafted in the liver, as shown by albumin staining in mice receiving perinatal transfer of Rosa26 MAPCs. In contrast, BALB/c-SCID mice did not express albumin. The presence of MAPCs was confirmed by lacZ-fluorescein isothiocyanate (FITC) staining. In the brain, NF-200 staining was negative, indicating that MAPCs did not differentiate into neurons. However, GFAP staining was very bright, confirming the presence of astrocyte cell types. MAPC engraftment was also observed in the lung by lacZ-FITC staining; however, these cells were negative for cytokeratin, indicating that IUT transfer of MAPCs did not result in differentiation to an epithelial cell type. Similar to lung engraftment, MAPCs were present in the intestine: however, cytokeratin staining was also negative, indicating that the MAPCs did not differentiate into intestinal epithelia. MAPCs were also found in the cardiac and skeletal muscle, as well as in the spleen and skin.

Total C57BL/6J-rosa26 MAPC engraftment in individual tissues was measured using quantitative PCR (ABI PRISM 7700 Sequence Detector with Sequence Detector Software 1.6, Applied Biosystems) for $Neo^R$ gene. Reaction conditions for amplification of $Neo^R$ gene were as follows: 40 cycles of a two step PCR (95° C. for 15 seconds, 60° C. for 60 seconds) after initial denaturation (95° C. for 10 minutes) with 2 µl of a DNA solution, 1×SYBR Green PCR Master Mix (Applied Biosystems), and 150 nM of each primer. The $Neo^R$ PCR primers were designed using the PrimerExpress software version 1.0 (Perkin Elmer/Applied Biosystems) as follows: $Neo^R$-forward: TGGATTGCACGCAGGTTCT (SEQ ID NO:1), $Neo^R$-reverse: TTCGCTTGGTGGTC-GAATG (SEQ ID NO:2). Reaction conditions for amplification of the control housekeeping GAPDH gene were as follows: 40 cycles of a two step PCR (95° C. for 15 sec, 60° C. for 60 see) after initial denaturation (95° C. for 10 minutes) with 2 µl of a DNA solution, 1×SYBR Green PCR Master Mix (Applied Biosystems), and 100 nM of each primer (Applied Biosystems). The results are provided in Table 7.

TABLE 7

Quantitative PCR of MAPC Engraftment in BALB/c-SCID mice

| Tissue | Average (% MAPC) | Range (% MAPC) | No. of Animals |
|---|---|---|---|
| Skeletal Muscle | 3 | 0.7-5 | 4 |
| Liver | 1.1 | 0.1-3 | 3 |
| Lung | 1 | 0.2-4.5 | 6 |
| Intestine | 0.35 | 0.1-1 | 4 |
| Bone marrow | 0.35 | 0.3-0.4 | 2 |
| Brain | 0.3 | 0.1-0.7 | 4 |
| Heart | 0.25 | 0.1-0.5 | 5 |
| Gonad | 0.2 | 0.1-0.3 | 2 |

$Neo^r$ amplification was normalized to Rosa26 MAPCs and the glyceraldehyde-3-phosphate dehydrogenase gene amplification for each sample.

Example 2: MAPC Infusion in a Murine Model of Hurler's Syndrome

Mice deficient in α-L-iduronidase ($IDUA^{-/-}$; MPS-1H) have no detectable IDUA, have an increased level of GAGs leading to skeletal and CNS abnormalities, and exhibit progressive coarseness. MAPCs were isolated from C57BL/6J-Rosa26 mice essentially as described in Example 1 and injected into control or MPS-1H mice at either embryonal day E15/16 or postnatal days 1-3 (dose for E15/16: 1 million cells/fetus, dose for postnatal: either 215,000 or 450,000 cells/gram of body weight). MAPCs were allowed to home to tissues for 10, 20, and 30 weeks.

Urine was collected weekly from 11 to 25 weeks to measure GAG excretion. Newborn day 2/3 MPS-1H MAPC recipients (n=6) showed significantly decreased excretion of GAG (p<0.05) compared to age-matched newborn MPS-1H mice (n=5) (FIG. 1). Treated mice were sacrificed at 10, 20, and 30 weeks post-natally, and various tissues were measured for GAG levels and IDUA levels. A colorimetric assay was used to measure GAG levels in urine. Approximately 15 µl of undiluted urine was aliquoted, followed by 35 µl of $dH_2O$, 100 µl of picric acid solution (comprising a 1:10 dilution of picric acid), 100 µl of a 7.5 g/L NaOH solution. Each sample was mixed by inversion and vortexed for 20 minutes. Color developed after 20 minutes, and 200 µl of the sample solution was transferred to a 96-well plate. Absorbance was monitored at λ=530 nm on a Bioscan Chameleon spectrophotometer. GAG levels in urine were assessed and normalized to creatinine values for each urine sample.

Tissue GAGs were detected in tissue homogenates using 1,9 dimethylmethylene blue dye-binding calorimetric assay, and normalized to total protein content. Tissue homogenate samples were diluted 1:10 in 0.24 M guanidinium hydrochloride. When urine was assayed, urine was also diluted in 0.24 M guanidinium hydrochloride. Samples were aliquoted to a 96-well plate, and 200 µl of DMMB dye (16 mg of 1,9-dimethylmethylene blue chloride in 5 ml of 95% ethanol; 2 ml of formic acid and 2 g of sodium formate added to 1 L dH20; DMMB solution is added to the formate solution) was added to the samples. The samples were read at λ=550 nm and then subsequently at λ=650 run. All values were subtracted from the blank solution, and normalized against standards of known concentration. The adjusted absorbance was then calculated by subtracting $A_{550}$ from $A_{650}$.

Average GAG values normalized to MPS-1H control mice were significantly decreased in both fetal and newborn MPS-1H MAPC recipients in many tissues. In each tissue studied, GAG content was reduced in MPS-1H+MAPCs, compared to MPS-1H controls, approaching or reaching levels of C57BL/6 mice in lung, muscle, spleen, ileum, and brain. Lesser effects were observed in kidney, liver, and colon.

Figure 2A:
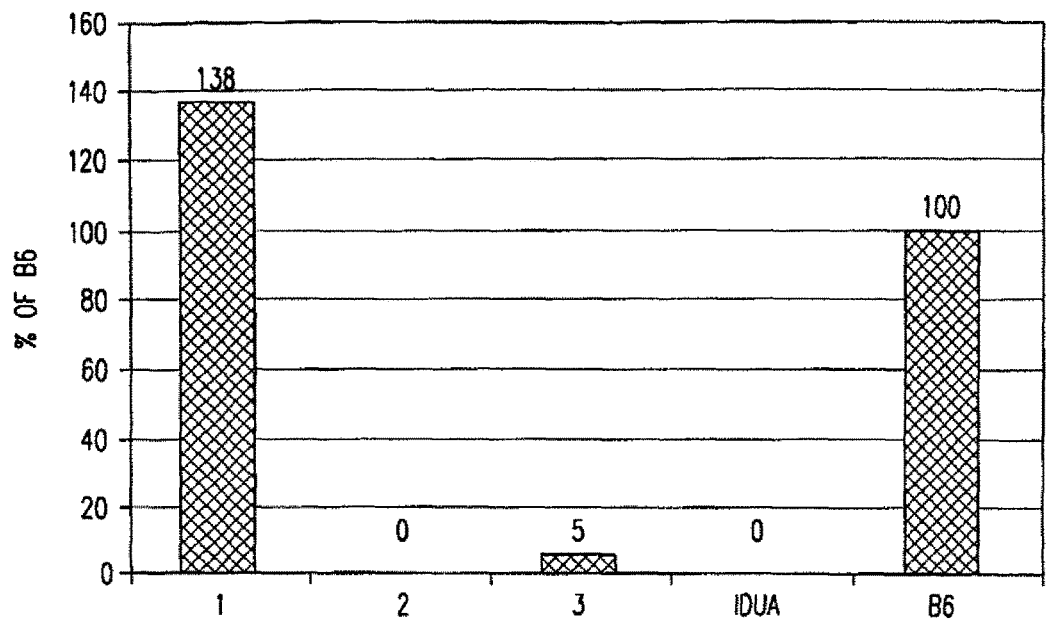
FIG. 2A-B shows a graph of α-L-iduronidase levels (FIG. 2A) and liver GAG accumulation (FIG. 2B) in B6, MPS-1H mice, and MPS-1H mice receiving in utero MAPC infusion.
Figure 2B:
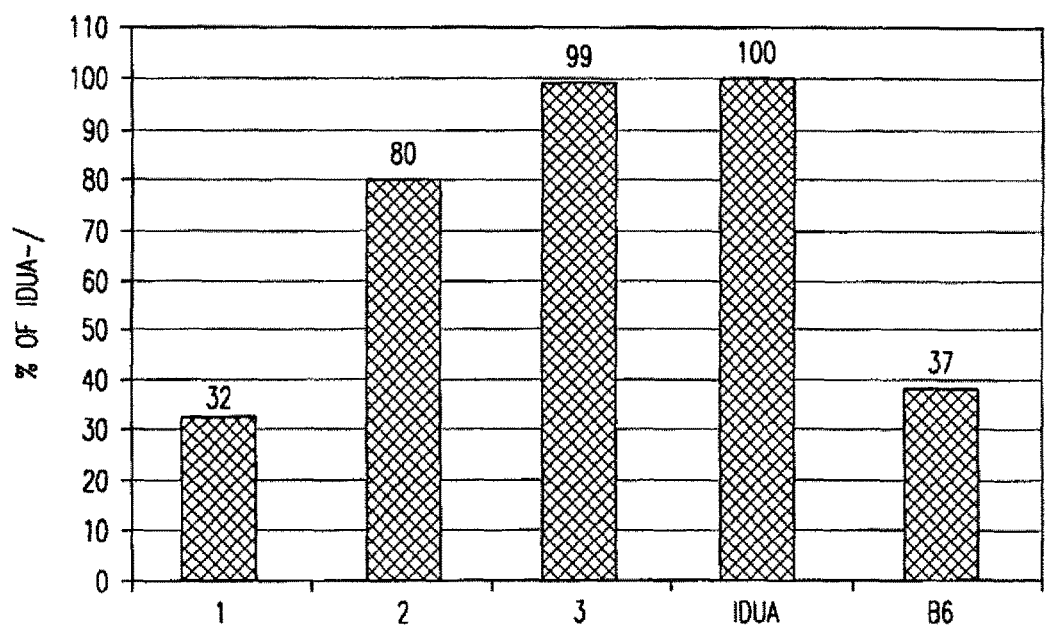
Figure 3:
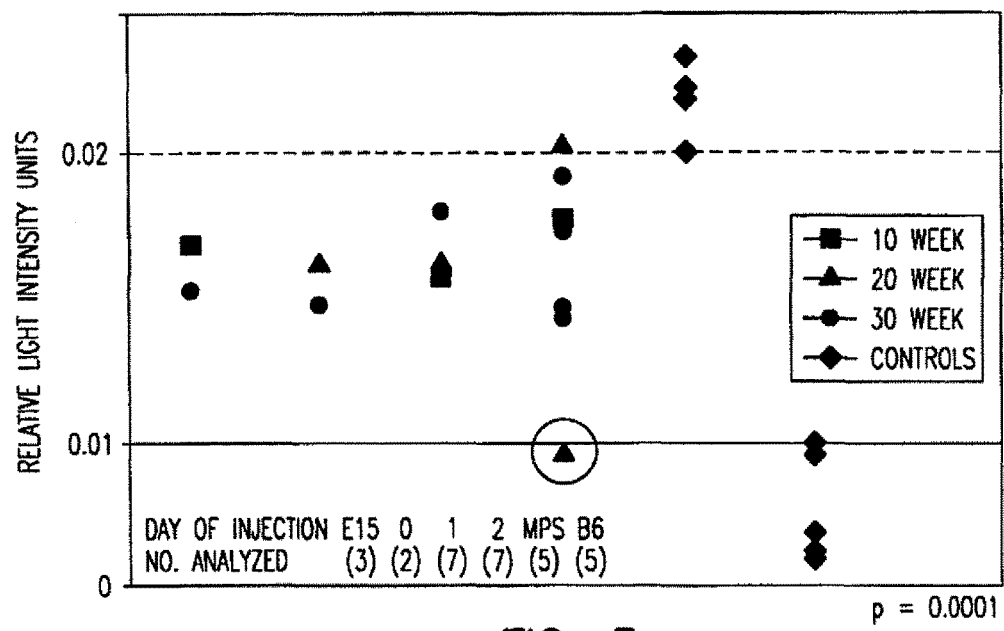
FIG. 3 is a dot graph of liver GAG accumulation in B6 and MPS-1H mice receiving in utero MAPC infusion.
Figure 6:
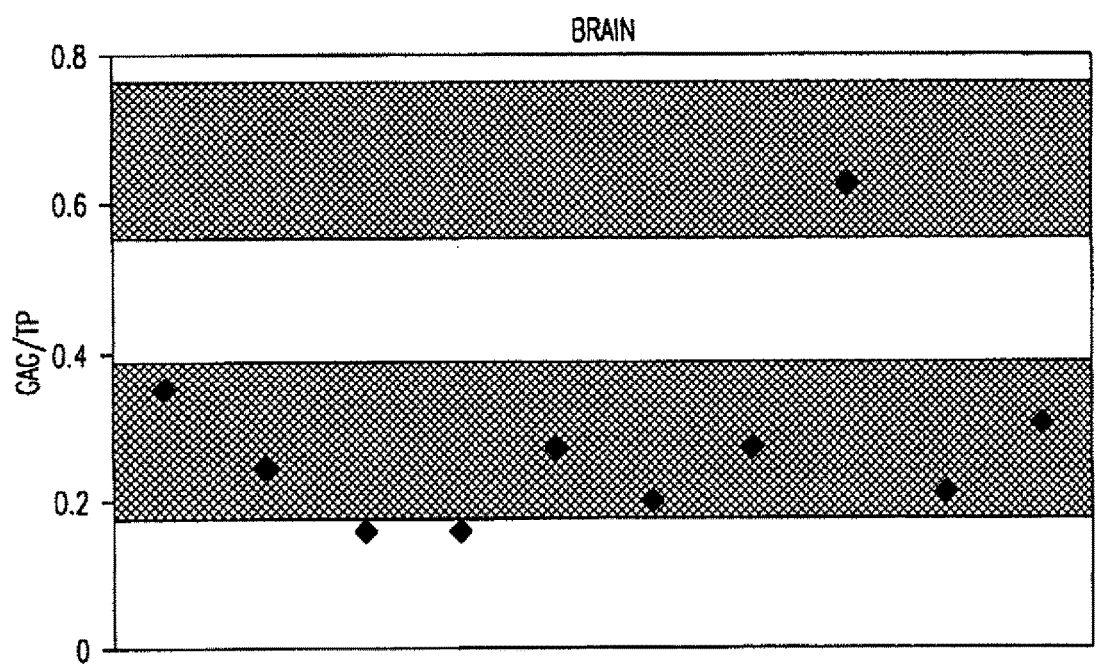
FIG. 6 is a graph depicting a decrease in GAG levels in brain of MPS-1H mice receiving in utero MAPC infusion. GAG per total protein (TP) (y-axis) from individual mice (listed on the x-axis) are depicted; range MPS-1H (DUA−/−) mice in light patterned region and B6 WT controls in grey shaded region. All but one MAPC treated mice had normal brain GAG levels.
Figure 7:
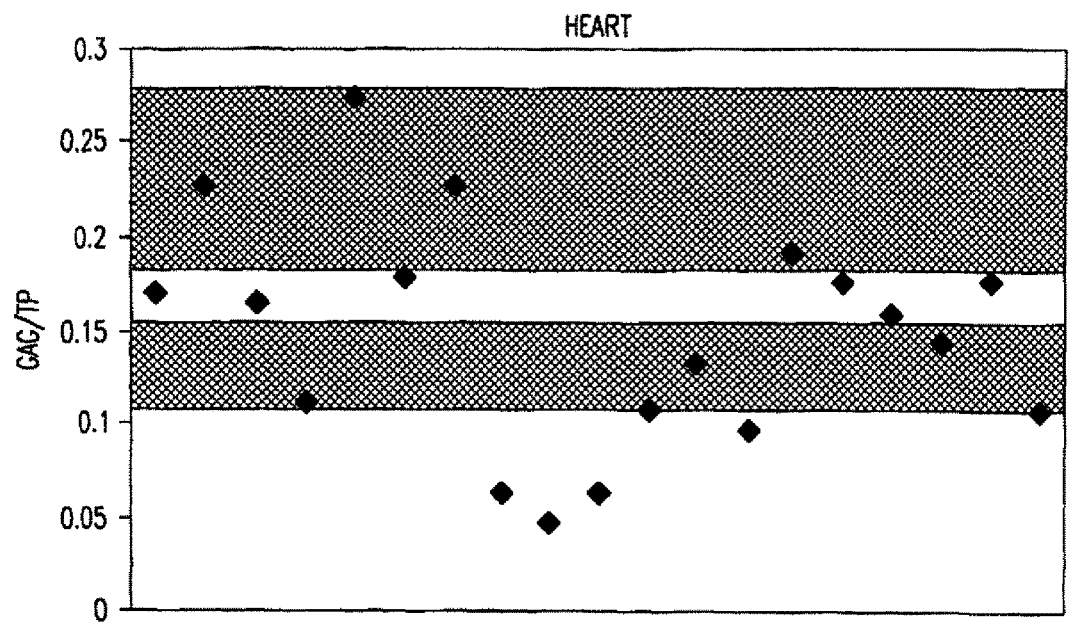
FIG. 7 is a graph depicting a decrease in GAG levels in heart of MPS-1H mice receiving in utero MAPC infusion. GAG per total protein (TP) (y-axis) from individual mice (listed on the x-axis) are depicted; range MPS-1H (DUA−/−) mice in light patterned region and B6 WT controls in grey shaded region. Heart GAGs were <MPS-1H levels in most mice with ~50% having values that did not exceed the WT control.
Figure 8:
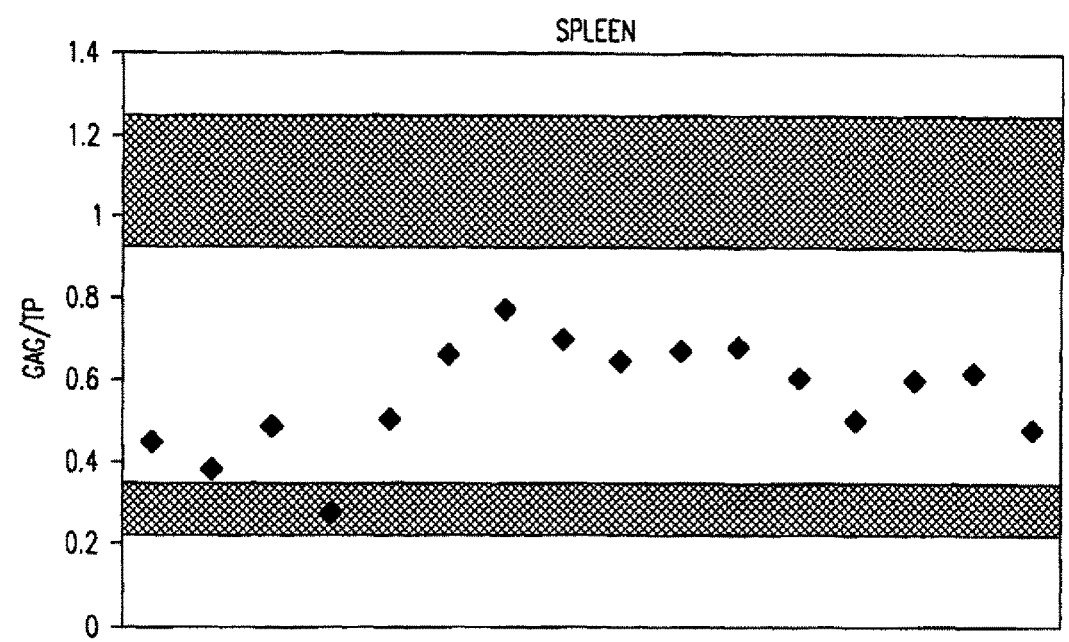
FIG. 8 is a graph depicting a decrease in GAG levels in spleen of MPS-1H mice receiving in utero MAPC infusion. GAG per total protein (TP) (y-axis) from individual mice (listed on the x-axis) are depicted; range MPS-1H (DUA−/−) mice in light patterned region and B6 WT controls in grey shaded region. Spleen GAGs were reduced to levels between MPS-1H and WT controls.

Decreased accumulation of GAGs in liver from mice infused with MAPCs in utero is depicted in graphical format (FIGS. 2 and 3). IDUA levels were also observed as depicted in FIG. 2. Additionally, decreased accumulation of GAG in brain, heart, and spleen from MPS-1H mice infused with MAPC is also depicted in graphical format (FIGS. 6, 7 and 8). Tissue lysates were prepared by first weighing the tissue, and then homogenizing the tissue in cryotubes. The homogenate was centrifuged and 50 µL of the supernatant was added to 50 µL of DH2O in 1.5 mL Eppendorf tubes. 1 mL of DMMB Dye was then added. The samples were vortexed for 30 minutes and then centrifuged for 10 minutes (10,4000 rpm). The dye was drained and the pellet was resuspended by the Dissociation Reagent (Blyscan) to release the unbound dye. 200 µL aliquots of each sample were added to 96 well plate wells (in triplicate). To detect the level of GAG in tissue, the samples were read at 650 nm ABS on a Bioscan Chameleon Platereader. Where plasma or blood samples were used, 3 ml of RPMI medium with 5% FBS was added to 0.5 ml of blood, and centrifuged for 30 seconds at 15,000 rpm. The top layer was extracted and used subsequently in IDUA assays.

For IDUA assays, tissue lysates were diluted 1:10 in lysate buffer, which comprises 0.02M Tris base, 0.25M NaCl, and 0.1M dithiothreitol (DTT) at pH7.4. Substrate solution was prepared by first making a 2× dilution buffer containing 42 mg of BSA, 6 ml of 0.1 M dimethylglutarate (DMG), and 12 µl of 1.0M sodium metabisulfite. The substrate stock comprises 2 mg of L-4-methylumbelliferyl-α-L-iduronide cyclohexylammonium salt dissolved in 0.1M dimethylglutarate buffer. The substrate stock was then added to 250 µl of 2× dilution buffer. All tissue lysates were placed on ice, then aliquoted to the substrate solution. The samples were then incubated in a 37° C. water bath. The reaction was stopped by adding 1400 µl of glycine buffer (dissolved 15 g of glycine and 13.25 g of $Na_2CO_3$ in 1 L of $dH_2O$, pH adjusted to 10.7 with NaOH). Each sample was then added to a black, flat-bottom 96-well plate and the fluorescence was detected on a Bioscan Chameleon plate reader, excitation=360 nm and emission at 425 nm.

Figure 4:
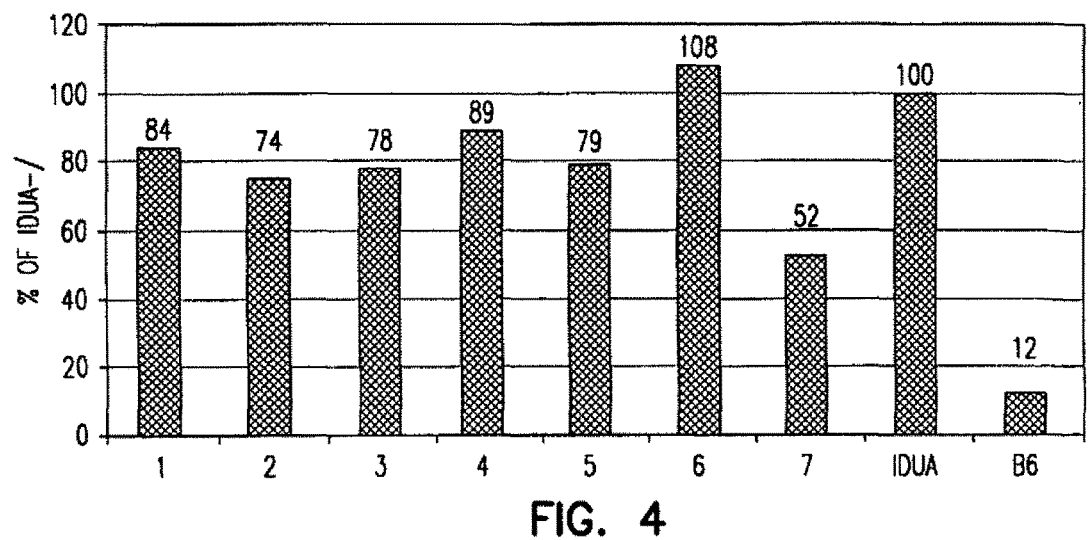
FIG. 4 is a bar graph depicting liver GAG accumulation in B6 and MPS-1H mice receiving post-natal MAPC infusion.

As shown in FIG. 3, each dot represents a value in one animal, grouped by tissue. Control animals are represented by black diamonds on the right-hand portion of the graph. Lines are drawn at the level of highest accumulation in 136 and the lowest accumulation in the MPS-1H mouse. Symbols (square, circle, triangle) refer to the age of the experimental animals at the time of sacrifice. Values are % of $IDUA^{-/-}$ or the wild-type control. MAPCs were administered at $10^6$ cells/fetus, and injected at embryonic day 15/16. Similar reductions in liver GAGs were seen when MAPCs were infused post-natally in MPS-1H mice (FIG. 4). Values are represented at % of $IDUA^{-/-}$ control (n=5), p=0.027. MAPC were administered at a dose of $0.215 \times 10^6$ or $0.45 \times 10^6$ cells/gram of body weight at post-natal days 1-3.

Figure 5:
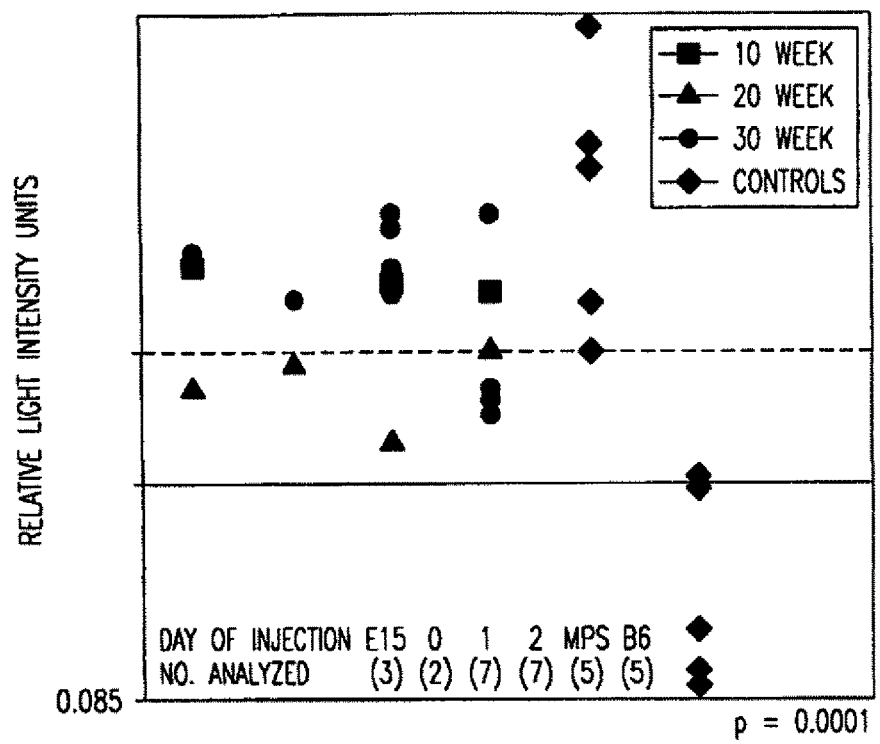
FIG. 5 is a dot graph of cardiac GAG accumulation in B6 and MPS-1H mice receiving in utero MAPC infusion.

GAG accumulation was also assessed in cardiac tissues (FIG. 5). As above, each dot represents a value in one animal, grouped by tissue. Control animals are shown on the right as black diamonds. Lines are drawn at the level of highest accumulation in 136 and the lowest accumulation in the MPS-1H mouse. Symbols (square, circle, triangle) refer to the age of the experimental animals at the time of sacrifice.

Additionally, echocardiograms were performed to assess cardiac function. In comparison to B6 controls, MPS-1H mice displayed a significant decrease in left ventricular end diastolic diameter and % fractional shortening and an increase in left ventricular mass, indicative of poor myocardial contractility. Further, aortic insufficiency (determined by abnormal flow detected on echocardiogram) was seen in MPS-1H mice (10 of 10), but not in B6 controls. M-mode ECHO showed cardiac dysfunction associated with thickened cardiac walls of MPS-1H mice vs. 136 controls. GAG accumulation in heart tissue of MPS-1H mice, but not in heart tissue of control B6 mice, was determined by immunohistochemistry. MAPC infusion decreased the incidence of aortic insufficiency. In fact, 6 out of 11 experimental mice had no aortic insufficiency (Table 8).

TABLE 8

|  | MAPC Infusion | N | Aortic Insufficiency |
|---|---|---|---|
| MPS-1H |  | 10 | 10 |
| C57BL/6J |  | 10 | 0 |
| MPS-1H | Day 0-2 | 6 | 2 |
| MPS-1H | Week 10-17 | 5 | 3 |

In addition, MAPC engraftment was assayed by immunohistochemistry. Tissue specimens of the recipient animals were cryopreserved in OCT at −80° C. Fresh frozen sections of approximately 6 µm thick were mounted on glass slides, fixed in acetone for 10 minutes at room temperature and incubated in isotype sera for 20 minutes. Cryosections were stained for β-galactosidase (fluorescein isothiocyanate (FITC)-coupled anti-β-galactosidase antibody, Rockland Immunochemicals) to assess exact histological location of the C57BL/6J-rosa26 MAPC-derived cells in the recipients.

Tissues were also examined for the tissue-specific characteristics of the C57BL/6J-rosa26 MAPC-derived cells by dual color immunofluorescence, using FITC-coupled anti-β-galactosidase antibody along with an antibody for one of the following tissue specific antigens. Pan-cytokeratin was used for pulmonic and colonic epithelium, albumin and cytokeratin-18 for liver, anti-mouse IgG Cy3 conjugate (all from Sigma), and nuclear counter stain (yoyo-1, PI). Between steps, slides were washed in PBS. Slides were examined by confocal, fluorescence microscopy (Olympus AX70, Olympus optical Co. LTD, Japan). Z-stack series in 3D reconstruction of confocal images were used to distinguish true positive cells from a simple overlay of two separate cells (negative control: propidium iodide and lacZ staining of MPS-1H liver tissues; positive control: Rosa 26 livers). Perinatal infusion of Rosa 26 MAPCs in MPS-1H mice showed significant engraftment by β-galactosidase staining. In lung tissues, MPS-1H negative control mice had dim β-gal expression, whereas Rosa 26 mice had bright staining for β-gal. Nuclei were stained with the DNA-specific dye, Yoyo-1® (Molecular Probes). MAPCs administered perinatally show engraftment in the lungs.

Additionally, total C57BL/6J-rosa26 MAPC engraftment in individual tissues was measured using quantitative PCR (ABI PRISM 7700 Sequence Detector with Sequence Detector Software 1.6, Applied Biosystems) for the LacZ gene. The forward primer sequence for the lacZ gene is as follows: 5'-AAA CCA GCC ATC GCC ATC TG-3' (SEQ ID N0:3). The reverse primer sequence is: 5'-GGA CAG GTC GGT CTT GAC AAA AAG-3' (SEQ ID N0:4). The PCR conditions comprised 34 cycles of 94° C. for 30 seconds, 58° C. for 30 seconds, and 72° C. for 60 seconds.

Although it is not meant as a limitation of the invention, it is believed that tissue injury may provide inductive signals or a permissive environment to attract MAPCs and facilitate their survival and expansion. $10^6$ MAPCs transgenic for luciferase and DsREd2 were injected via a facial vein on day 4 of age into MPS-1H pups. The mice were imaged weekly 5 minutes after intraperitoneal injection of luciferin. Luminescence activity was analyzed using Xenogen IVIS Imaging System and pseudo color scheme was used to display the lucerferase activity. The results of real time tracking of MAPC in MPS-1H mice demonstrates that MAPCs increased in number between 7 and 14, in contrast to WT (control) mice. Therefore, abnormal levels of GAG in tissues may support MAPC engraftment.

The foregoing specification has been described in relation to certain embodiments thereof, and many details have been set forth for purposes of illustration, however, it will be apparent to those skilled in the art that the invention is susceptible to additional embodiments and that certain of the details described herein may be varied considerably without departing from the basic principles of the invention.

Each of the applications and patents cited in this text, as well as each document cited in each of the applications and patents (including during the prosecution of each issued patent; "application cited documents"), and each of the PCT and foreign applications or patents corresponding to and/or claiming priority from any of these applications and patents, and each of the documents cited in each of the application cited documents, are hereby expressly incorporated herein by reference. More generally, documents are cited in this text, either in a Bibliography, or in the text itself; and, each of these documents, as well as each document cited therein (including any manufacturer's specifications, instructions, etc.), is hereby expressly incorporated herein by reference. Reference is specifically made to International Application Nos. PCT/US00/21387, filed on Aug. 4, 2000 (published as WO 01/110011 on Feb. 15, 2001), and PCT/US02/04652, filed on Feb. 14, 2002 (published as WO 02/064748 on Aug. 22, 2002), the contents of which are incorporated in their entirety herein by reference.

BIBLIOGRAPHY

All cited documents are incorporated by reference as though fully set forth herein.

Barker, J. E., Deveau, S., Lessard, M., Hamblen, N., Vogler, C. Levy, B.: "In utero fetal liver cell transplantation without toxic irradiation alleviates lysosomal storage in mice with mucopolysaccharidosis type VII" (2001) Blood Cells Mol. Dis. 27: 861-873.

Basch, R. S., Berman, J. W., Lakow, E.: "Cell separation using positive immunoselective techniques" (1983) J. Immunol. Methods 56(3): 269-80.

Batinic, D., Marusic, M., Pavletic, Z., Bogdanic, V., Uzarevic, B., Nemet, D., Labar, B.: "Relationship between differing volumes of bone marrow aspirates and their cellular composition". (1990) Bone Marrow Transplant. 6(2): 103-7.

Caillaud, C., and Poenaru, L.: "Gene therapy in lysosomal diseases" (2000) Biomed. Pharmacother. 54: 505-12.

Capecchi, M. R.: "Altering the genome by homologous recombination" (1989) Science 244: 1288-1292.

Capecchi, M. R.: "The new mouse genetics: altering the genome by gene targeting" (1989) Trends Genet. 5(3): 70-76.

Carrier, E., Lee, T. H., Busch, M. P., Cowan, M. J.: "Induction of tolerance in nondefective mice after in utero transplanatation of major histocompatibility complex-mismatched fetal hematopoietic stem cells" (1995) Blood 86: 4681-4690.

Carrier, E., Lee, T. H., Busch, M. P., Cowan, M. J.: "Recruitment of engrafted donor cells postnatally into the blood with cytokines after in utero transplantation in mice" (1997) Transplantation 64: 627-633.

Casal, M. L. and Wolfe, J. H.: "Mucopolysaccharidosis type VII in the developing mouse fetus" (2000) Pediatr. Res. 47: 750-6.

Casal, M. L. and Wolfe, J. H.: "In utero transplantation of fetal liver cells in the mucopolysaccharidosis type VII mouse results in low-level chimerism, but overexpression of β-glucuronidase can delay onset of clinical signs" (2001) Blood 97: 1625-1634.

Cheng, S. H., and Smith, A. E.: "Gene therapy progress and prospects: gene therapy of lysosomal storage disorders" (2003) Gene Ther. 10: 1275-1281.

Donahue, J., and Carrier, E.: "Non-myeloablative transplants for congenital diseases". (2002) Cancer Treat Res 110: 177-211.

Du, H., Heur, M., Witte, D. P., Ameis, D., Grabowski, G. A.: "Lysosomal acid lipase deficiency: correction of lipid storage by adenovirus-mediated gene transfer in mice". (2002) Hum. Gene Ther. 13(11): 1361-72.

Flake, A. W. and Zanjani, E. D.: "In utero hematopoietic stem cell transplantation: ontogenic opportunities and biologic barriers" (1999) Blood 94: 2179-2191.

Frisella, W. A., O'Connor, L. H., Vogler, C. A., Roberts, M Walkley, S., Levy, B., Daly, T. M., Sands, M. S.: "Intracranial injection of recombinant adeno-associated virus improves cognitive function in a murine model of mucopolysaccharidosis type VII." (2001) Mol Ther. 3(3): 351-8.

Hoogerbrugge, P. M., Brouwer, O. F., Bordigoni, P., Ringden, O., Kapaun, P., Ortega, J. J., O'Meara, A., Cornu, G., Souillet, G., Frappaz, D., Blanche, S., Fischer, A.: "Allogeneic bone marrow transplantation for lysosomal storage diseases. The European Group for Bone Marrow Transplantation" (1995) Lancet. 345(8962): 1398-402.

International Application PCT/US00/21387, published as WO 01/11011, filed in U.S. as Ser. No. 10/048,757

International Application PCT/US02/04652, published as WO 02/064748, filed in the U.S. as Ser. No. 10/467,963

Jiang, Y., Jahagirdar, B. H., Reinhardt, R. L., Schwartz, R. E., Keene, C. D., Ortiz-Gonzalez, X. R., Reyes, M., Lenvik, T., Lund, T., Blackstad, M., Du, J., Aldrich. S., Lisberg, A., Low, W. C., Largaespada, D. A., Verfaillie, C. M.: "Pluripotency of mesenchymal stem cell derived from adult marrow" (2002) Nature 418: 41-49.

Lewin, B., Genes V, Oxford University Press, New York (1994), pp. 968-997.

Lutzko, C., Omori, F., Abrams-Ogg, A. C. G., Shull, R., Li, L., Lau, K., Ruedy, C., Nanji, S., Gartley, C., Dobson, H., Foster, R. Kruth, S., and Dube, I. D.: "Gene therapy for canine α-L-iduronidase deficiency: in utero adoptive transfer of genetically corrected hematopoietic progenitors results in engraftment but not amelioration of disease" (1999) Hum. Gene Ther. 10: 1521-1532.

Marshall, J., McEachem, K. A., Kyros, J. A., Nietupski, J. B., Budzinski, T., Ziegler, R. J., Yew, N. S., Sullivan, J., Scaria, A., vanRooijen, N., Barranger, J. A., Cheng, S. H.: "Demonstration of feasibility of in vivo gene therapy for Gaucher disease using a chemically induced mouse model". (2002) Mol. Ther. 6(2): 179-89.

Muschler, G. F., Boehm, C., Easley, K.: "Aspiration to obtain osteoblast progenitor cells from human bone marrow: the influence of aspiration volume". (1997) J. Bone Joint Surg. Am. 79(11): 1699-709.

Nathan, D. G.: "Storage Diseases of the Reticuloendothelial System" In: Nathan, D. G., Orkin, S. H., Ginsburg, D., Look, A. T., Oski, F. A., Magee, D. J. (eds) *Nathan and Oski's Hematology of Infancy and Childhood*, 6th edition (2003) W.B. Saunders, p. 1408-1426

Peters, C., Balthazor, M., Shapiro, E. G., King, R. J., Kallman, C., Hegland, J. D., Henslee-Downey, J., Trigg, M. E., Cowan, M. J., Sanders, J., Bunin, N., Weinstein, H., Lenarsky, C., Falk, P., Harris, R., Bowen, T., Williams, T. E., Grayson, G. H., Warkentin, P., Sender, L., Cool, V. A., Crittenden, M., Packman, S., Kaplan, P., Lockman, L. A.: 'Outcome of unrelated donor bone marrow transplantation in 40 children with Hurler syndrome' (1996) Blood 87(11): 4894-902.

Peters, C., Shapiro, E. G., Anderson, J., Henslee-Downey, P. J., Klemperer, M. R., Cowan, M. J., Saunders, E. F., deAlarcon, P. A., Twist, C., Nachman, J. B., Hale, G. A., Harris, R. E., Rozans, Kurtzberg, J., Grayson, G. H., Williams, T. E., Lenarsky, C., Wagner, J. E., Krivit, W.: "Hurler syndrome: II. Outcome of HLA-genotypically identical sibling and HLA-haploidentical related donor bone marrow transplantation in fifty-four children. The Storage Disease Collaborative Study Group." (1998) Blood 91(7): 2601-8.

Remington, J. P.: Remington's Pharmaceutical Sciences 18th edition (1990) Mack Publishing Company.

Schiffmann, R., Kopp, J. B., Austin III, H. A., Sabnis, S., Moore, D. F., Weibel, T., Balow, J. E., Brady, R. O.: "Enzyme Replacement Therapy in Fabry Disease: A Randomized Controlled Trial" (2001) JAMA 285: 2743-2749.

Schlossman, S.: "Leucocyte Typing V: White Cell Differentiation Antigens" Oxford University Press, (1995).

Schwartz, R. M., Elkalay; M. A.: U.S. Pat. No. 5,759,793

Scott, H. S., Bunge, S., Gal, A., Clarke, L. A., Morris, C. P., and Hopwood, J. J. "Molecular genetics of mucopolysaccharidosis type I: diagnostic, clinical, and biological implications". (1995) Hum Mutat 6: 288-302.

Steward, C. G.: "Bone marrow transplantation for genetic diseases". In: Fairbairn, L. J., Testa, N. G. (eds) *Blood Cell Biochemist!)'—Volume* 8: *Hematopoiesis and Gene Therapy* (1999) New York: Klewer Academic/Plenum. Publishers. p. 13-56.

Surbek, D. V., Young, A., Danzer, E., Schoeberlein, A., Dudler, L., Holzgreve, W.: "Ultrasound-guided stem cell sampling from the early ovine fetus for prenatal ex vivo gene therapy" (2002) Am. J. Obstet. Gynecol. 187: 960-3.

Suzuki, K.: "Lysosomal Diseases". In: Graham, D. I., Lantos, P. K. (eds) *Greenfield's Neuropathology*. Arnold: London (2002) pp. 653-735.

Wraith, J. E.: "Advances in the treatment of lysosomal storage diseases" (2001) Dev. Med. Child Neural. 43: 639-646.

Weinreb, N. J., Charrow, J., Andersson, H. C., Kaplan, P., Kolodny, E. H., Mistry, P., Pastores, G., Rosenbloom, B. E., Scott, C. R., Wappner, R. S., and Zimran, A.: "Effectiveness of enzyme replacement therapy in 1028 patients with type 1 Gaucher disease after 2 to 5 years of treatment: a report from the Gaucher Registry" (2002) Am. J. Med. 113(2): 112-9.

Wolff, J. A.: Gene Therapeutics: Methods and Applications of Direct Gene Transfer, 1st edition Birkhauser Publishing, Boston, Mass., (1995) p. 195.

Wysocki, L. J., Sato, V. L.: "'Panning' for lymphocytes: a method for cell selection". (1978) Proc. Natl. Acad. Sci. USA. 75(6): 2844-8.

What is claimed is:

1. A method for treating a lysosomal storage disorder comprising administering stem cells to a subject having a lysosomal storage disorder, wherein the stem cells are isolated expanded human non-embryonic stem, non-germ cells that express telomerase, have undergone about 10-40 doublings in culture, and can differentiate into cell types of at least two of the endodermal, ectodermal, and mesodermal lineages, and wherein the stem cells naturally express an amount of lysosomal enzyme effective to treat said disorder, wherein the non-embryonic non-germ non-embryonic germ cells are derived from bone marrow.

2. The method of claim 1, wherein the lysosomal storage disorder is selected from the group consisting of sphingolipidoses, mucopolysaccharidoses, glycoproteinoses, mucolipidoses, glycogenosis type II and ceroid lipofuscinoses.

3. The method of claim 1, wherein the lysosomal storage disorder is selected from the group consisting of GM1 gangliosidosis, GM2 gangliosidosis variant B/B1 and variant O, metachromatic leukodystrophy, Krabbe's disease, Fabry's disease, Gaucher's disease, Niemann-Pick disease, Farber's disease, Wolman's disease, Austin's disease, mucopolysaccharidoses type I, Scheie's disease, Hurler-Scheie's disease, Sanfilippo's disease, Morquio's disease, Maroteaux-Lamy's disease, Sly's disease, pycnodysostosis, aspartylglucosaminuria, fucosidosis, α-mannosidosis, β-mannosidosis, Schindler's disease, Kanzaki's disease, mucolipidoses type I, galactosialidosis, mucolipidoses, glycogenosis type II, Santavuori-Haltia disease, Jansky-Bielshowsky disease, Batten disease, Kufs disease, disease states characterized by mutations in the CLN5, CLN6, CLN7 and CLN8 loci, sialic acid storage diseases, Salla disease, and methylmalonic aciduria.

4. The method of claim 2, wherein the subject has mucopolysaccharidosis.

5. The method of claim 4, wherein the mucopolysaccharidosis is Hurler's disease.

6. The method of any of claims 1-5, wherein the non-embryonic, non-germ cells express one or more of oct4, rex-1, and rox-1.

7. The method of claim 1, wherein the stem cells are administered by a method selected from the group consisting of localized injection, catheter administration, systemic injection, intraperitoneal injection, intraplacental injection, intrauterine injection, intracranial injection, parenteral administration, intraarterial injection and injection into the lateral cerebral ventricles.

* * * * *